(12) United States Patent  
Tada et al.

(10) Patent No.: US 9,192,693 B2  
(45) Date of Patent: *Nov. 24, 2015

(54) METHOD FOR TREATMENT OF EMPHYSEMA

(75) Inventors: Yuichi Tada, Ashigarakami-gun (JP); Takao Anzai, Ashigarakami-gun (JP); Atsuhiko Nogawa, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1127 days.

This patent is subject to a terminal disclaimer.

(21) Appl. No.: 13/216,912

(22) Filed: Aug. 24, 2011

(65) Prior Publication Data

US 2012/0053513 A1  Mar. 1, 2012

Related U.S. Application Data

(60) Provisional application No. 61/376,825, filed on Aug. 25, 2010.

(51) Int. Cl.  
*A61M 16/04* (2006.01)  
*A61M 25/10* (2013.01)  
(Continued)

(52) U.S. Cl.  
CPC .............. *A61L 24/104* (2013.01); *A61K 9/007* (2013.01); *A61L 24/06* (2013.01); *A61L 24/08* (2013.01);  
(Continued)

(58) Field of Classification Search  
CPC ................... A61B 17/12104; A61B 17/12022; A61B 1/2676; A61B 17/12136; A61M 16/04; A61M 2025/1052; A61M 16/0404; A61M 2202/0007; A61M 2202/0208; A61M 2202/0225; A61M 2202/0488; A61M 2202/064; A61M 2210/1039; A61K 9/007; A61L 24/104; A61L 24/06; A61L 24/08  
USPC ............... 604/26–28, 96.01, 98.01, 264, 275, 604/507–509  
See application file for complete search history.

(56) References Cited

U.S. PATENT DOCUMENTS 5,575,815 A   11/1996   Slepian et al.  
6,258,100 B1   7/2001   Alferness et al.  
(Continued)

FOREIGN PATENT DOCUMENTS

JP   09-506011 A   6/1997  
JP   2003-503162 A   1/2003  
(Continued)

OTHER PUBLICATIONS

International Search Report (PCT/ISA/210) issued on Nov. 15, 2011 by the Japan Patent Office in corresponding PCT International Application No. PCT/JP2011/068318, with an English translation thereof.  
(Continued)

*Primary Examiner* — Theodore Stigell  
*Assistant Examiner* — Lauren M Peng  
(74) *Attorney, Agent, or Firm* — Buchanan Ingersoll & Rooney PC

(57) ABSTRACT

Disclosed herein is a method for treatment of emphysema by reducing the volume of the pulmonary alveoli or alveolar sacs which have been anomalously expanded with destruction by emphysema. The method includes a step (a) of inserting a catheter into a bronchus or bronchiole, a step (b) of injecting through said catheter a film-forming agent into the respiratory region including the pulmonary alveoli or alveolar sacs, thereby forming a film on the inner wall of said respiratory region, and a step (c) of shrinking said pulmonary alveoli or alveolar sacs.

7 Claims, 13 Drawing Sheets

(51) Int. Cl.
  *A61K 9/00* (2006.01)
  *A61L 24/10* (2006.01)
  *A61L 24/06* (2006.01)
  *A61L 24/08* (2006.01)

(52) U.S. Cl.
  CPC ........... *A61M 16/04* (2013.01); *A61M 16/0404* (2014.02); *A61M 2025/1052* (2013.01); *A61M 2202/0007* (2013.01); *A61M 2202/0208* (2013.01); *A61M 2202/0225* (2013.01); *A61M 2202/0488* (2013.01); *A61M 2202/064* (2013.01); *A61M 2210/1039* (2013.01)

(56) References Cited

U.S. PATENT DOCUMENTS

| | | |
|---|---|---|
| 6,287,290 B1 | 9/2001 | Perkins et al. |
| 6,610,043 B1 * | 8/2003 | Ingenito ............ 604/514 |
| 6,682,520 B2 | 1/2004 | Ingenito |
| 7,300,428 B2 | 11/2007 | Ingenito |
| 7,468,350 B2 | 12/2008 | Gong et al. |
| 7,549,984 B2 | 6/2009 | Mathis |
| 7,553,810 B2 | 6/2009 | Gong et al. |
| 7,608,579 B2 | 10/2009 | Gong et al. |
| 7,654,998 B1 | 2/2010 | Ingenito |
| 7,654,999 B2 | 2/2010 | Ingenito |
| 7,678,767 B2 | 3/2010 | Gong et al. |
| 7,932,225 B2 | 4/2011 | Gong et al. |
| 2006/0264772 A1 | 11/2006 | Aljuri et al. |
| 2007/0110813 A1 | 5/2007 | Ingenito et al. |
| 2008/0097139 A1 * | 4/2008 | Clerc et al. ............ 600/7 |
| 2008/0261884 A1 | 10/2008 | Tsai et al. |
| 2008/0281352 A1 | 11/2008 | Ingenito et al. |
| 2009/0012626 A1 | 1/2009 | Thompson et al. |
| 2009/0076623 A1 | 3/2009 | Mathis et al. |
| 2009/0104183 A1 | 4/2009 | Gong et al. |
| 2010/0070050 A1 | 3/2010 | Mathis et al. |
| 2010/0297218 A1 | 11/2010 | Gong et al. |
| 2010/0305715 A1 | 12/2010 | Mathis et al. |
| 2013/0178426 A1 | 7/2013 | Anzai |

FOREIGN PATENT DOCUMENTS

| | | |
|---|---|---|
| JP | 2003507130 A | 2/2003 |
| JP | 2003518190 A | 6/2003 |
| JP | 2009504342 A | 2/2009 |
| JP | 2009-514860 A | 4/2009 |
| JP | 2009514860 A | 4/2009 |
| JP | 2010526914 A | 8/2010 |
| WO | 01/13908 A2 | 3/2001 |
| WO | 01/46327 A2 | 6/2001 |
| WO | 2007/022377 A2 | 2/2007 |
| WO | 2007/055950 A2 | 5/2007 |
| WO | 2008/141059 A2 | 11/2008 |
| WO | WO 2009/075106 A1 | 6/2009 |

OTHER PUBLICATIONS

Written Opinion of the International Searching Authority (PCT/ISA/237) issued on Nov. 15, 2011 by the Japan Patent Office in corresponding PCT International Application No. PCT/JP2011/068318, with an English translation thereof.

Ingenito et al., "*Bronchoscopic Lung Volume Reduction Using Tissue Engineering Principles*," American Journal of Respiratory and Critical Care Medicine, 2003 (month unkown), vol. 167, pp. 771-778.

Kaneko, "*Current State and Prospect of Fibrin Adhesive in Lung Surgery: 2 Spontaneous Pneumothorax and Pulmonary Emphysema*," Surgery Frontier, Sep. 1, 2001, vol. 8, No. 3, pp. 336-340, with an English translation.

Watanabe et al., "*Endoscopic Lung Volume Reduction for Severe Pulmonary Emphysema Using EWS*," The Journal of the Japanese Respiratory Society, Jun. 10, 2006, vol. 44, section PP224 of p. 290, with an English translation.

Jadranka Spahija et al., "Effects of Imposed Pursed-Lips Breathing on Respiratory Mechanics and Dyspanea at Rest and During Exercise in COPD", Chest, Aug. 2005; vol. 128, No. 2, pp. 640-650, American College of Chest Physicians.

Jan A. Van Noord et al., "Effects of Tiotropium With and Without Formoterol on Airflow Obstruction and Resting Hyperinflation in Patients With COPD", Chest, Mar. 2006; vol. 129, No. 3, pp. 509-517, American College of Chest Physicians.

JH Ware et al., "Cost Effectiveness of Lung-Volume-Reduction Surgery for Patients With Severe Emphysema", The New England Journal of Medicine, May 22, 2003; vol. 348; pp. 2092-2102.

National Emphysema Treatment Trial Research Group, "A Randomized Trial Comparing Lung-Volume-Reduction Surgery With Medical Therapy for Severe Emphysema", The New England Journal of Medicine, May 22, 2003; vol. 348, pp. 2059-2073.

Kobayashi H. and Kanoh S., "Bronchoscopic Autologous Blood Injection for Lung Volume Reduction*", Journal of Japanese Respiratory Society, 2009, vol. 47, No. 9, pp. 765-771.

Reilly J. et al., "Biological Lung Volume Reduction*", Chest, 2007 vol. 131, No. 4, pp. 1108-1113.

Official Reason for Rejection issued in Japan Appl. No. 2010-219330, dated Sep. 2, 2014.

Office Action issued in China Appl. No. 2011841265.0, dated Mar. 4, 2014.

* cited by examiner

METHOD FOR TREATMENT OF EMPHYSEMA

This application claims the benefit under 35 U.S.C. 119(e) of provisional Application No. 61/376825, filed Aug. 25, 2010.

BACKGROUND

1. Technical Field

The present invention relates to a method for treatment of emphysema. In particular, the present invention relates to a method for treatment of emphysema by reducing the volume of the pulmonary alveoli or alveolar sacs which have been anomalously expanded with destruction by emphysema.

2. Description of the Related Art

Among a large group of pulmonary diseases that hinder normal respiration is chronic obstruction pulmonary disease (COPD) which brings about lung occlusion on account of at least one disease selected from asthma, emphysema, and chronic bronchitis. COPD frequently involves these diseases at one time and makes it difficult to confirm in each case which one of them really causes the lung occlusion. A case is clinically diagnosed as COPD by constant decrease in expiration flow from the lung over several months, even more than two years for a case of chronic bronchitis. Two of the most critical states relating to COPD are chronic bronchitis and emphysema.

The emphysema denotes a state of anomalous expansion with destruction that occurs in the respiratory bronchioles which permit gas exchange and the tissue called alveolar parenchyma such as pulmonary alveoli, alveolar sac and the like. The alveolar parenchyma in its normal state shrinks at the time of expiration, but the one suffering from emphysema does not recover itself after expansion by respiration. This inhibits normal expiration. Moreover, emphysema decreases the effective area and vascular bed (which denotes capillary vessels running point to point on the surface of the pulmonary alveoli) of the pulmonary alveoli, thereby reducing the gas exchange capacity of the entire lung. In addition, emphysema involves inflammation that destroys elastin and collagen, thereby causing the lung to decrease in elasticity. The result is that the lung cannot keep stretching and expanding the respiratory tract, and this permits the bronchia to deform easily. As the result, the bronchus is compressed to become thin by its surrounding air-filled pulmonary alveoli as the lung shrinks at the time of expiration. This makes the lung expand excessively, preventing air from being discharged easily (see WO 2009/075106 A1, ST MARIANNA UNIVERSITY SCHOOL, MIYAZAWA TERUOMI, "STENT FOR TRATING CHRONIC OBSTRUCTIVE PULMONARY DISEASE"). For this reason, a patient of emphysema purses up his lips to expire (see Jadranka Spahija et al., "Effects of Imposed Pursed-Lips Breathing on Respiratory Mechanics and Dyspanea at Rest and During Exercise in COPD", Chest 2005; 128:640-650).

In Japan, there are about 50,000 patients with emphysema who are receiving home oxygen therapy, and it is estimated that about three million people including those of mild case are liable to emphysema. At present, the major method of therapy for emphysema is home oxygen therapy. Oxygen therapy is commonly used for the patient who cannot take in sufficient oxygen from air on account of his seriously damaged lung function. However, it merely relieves the patient's condition but it is not an effective method of therapy. On the other hand, there are several methods of pharmacotherapy including: administration of bronchodilator to open respiratory tracts in the lung, thereby alleviating breathing difficulties; administration of steroid by inhalation or mouth, thereby alleviating inflammation in respiratory tracts; administration of antibiotics to prevent or treat secondary infection; and administration of expectorant to remove mucus from respiratory tracts (see Jan A. van Noord et al., "Effects of Tiotropium With and Without Formoterol or Airflow Obstruction and Resting Hyperinflation in Patients With COPD", Chest 2006; 129:509-517). All of these pharmacotherapies help control emphysema and alleviate its symptom, but they are not necessarily effective. In addition, there are several methods of surgical treatment which include lung reductive surgery which removes damaged parts from the lung, thereby allowing the normal parts of the lung to expand and lung transplantation. However, these methods impose a heavy burden on patients and involved difficulties in securing the lung to be substituted (see Ware J H, et al., "Cost effectiveness of Lung-Volume-Reduction Surgery for Patients with Severe Emphysema", The New England Journal of Medicine 2003; 348: 2092-2102; National Emphysema Treatment Trial Research Group, "A Randomized Trial Comparing Lung-Volume-Reduction Surgery with Medical Therapy for Severe Emphysema", The New England Journal of Medicine 2003; 348: 2059-2073).

If it is possible to carry out "LVR (Lung Volume Reduction)" noninvasively without thoracotomy, many patients will have the chance of therapy. However, the current noninvasive therapy has a low success rate. For example, one of the non-invasive therapy which is expected to produce the same effect as "LVRS (Lung Volume Reduction Surgery)" is an indwelling device in which a one-way valve that prevents the entry of inspired gas into the lung end is left in the bronchus (see Alferness, Clifton A et al., Spiration, Inc., U.S. Pat. No. 6,258,100 B1). However, once left in the lung, it prevents access to any place beyond its indwelling point (see Mark L. Mathis, PneumRx, Inc., U.S. Pat. No. 7,549,984 B1).

It is known that there exists a passage for air flow called bypass, which is different from the main respiratory tract, in the damaged respiratory bronchioles and alveolar parenchyma. Therefore, even through the above-mentioned device prevents air from flowing through the main respiratory tract by the device, air gets around the obstruction by the device to reach the damaged respiratory bronchioles and alveolar parenchyma. Consequently, the above-mentioned device cannot prevent the expansion of the lung (see ALJURI NIKOLAI at al., PULMONX, US 2006/0264772 A1).

There is provided, as another non-surgical method of reducing the lung volume, a method which comprises collapsing a region of the lung and bonding a part of the collapsed region to another region of the lung and further promoting the growth of fiber in the bonded tissue or the vicinity thereof to realize LVR (see Edward P. Ingenito et al., Bistech, Inc., U.S. Pat. No. 6,682,520 B1). In this method, however, it needs a certain length of time for the lung parenchyma to be destroyed by the reaction of the living body. The U.S. Pat. No. 6,682,520 B1 further mentions a method for carrying out LVR by means of a material containing that part of the damaged lung tissue to which targeting therapy is applied. This method needs the part for targeting therapy and also needs a process in which the material reacts with the damaged part (see Gong; Glen et al., PneumRx, Inc., U.S. Pat. No. 7,678, 767 B1).

The foregoing suggests that there exists no effective method for treatment of emphysema at present, in the relevant field of art.

SUMMARY

It is an object of the present invention to provide a method for reducing the volume of the pulmonary alveoli or alveolar sacs suffering from emphysema.

According to one embodiment of the present invention, the method for treatment of emphysema comprises (a) inserting a catheter into a bronchus or bronchiole, (b) injecting through said catheter a film-forming agent into the respiratory region including the pulmonary alveoli or alveolar sacs, thereby forming a film on the inner wall of said respiratory region, and (c) shrinking said pulmonary alveoli or alveolar sacs.

The method according to the present invention can reduce less-invasively the volume of the pulmonary alveoli or alveolar sacs suffering from emphysema.

DETAILED DESCRIPTION OF THE PREFERRED EMBODIMENTS

According to the present invention, the method for treatment of emphysema comprises a step (a) of inserting a catheter into a bronchus or bronchiole, a step (b) of injecting through said catheter a film-forming agent into the respiratory region including the pulmonary alveoli or alveolar sacs, thereby forming a film on the inner wall of said respiratory region, and a step (c) of shrinking said pulmonary alveoli or alveolar sacs. Incidentally, the term "treatment" as used in this specification implies any medical practice to heal, alleviate, reduce, restore, prevent, or improve emphysema, symptoms of emphysema, or any symptoms that follow emphysema.

The present invention produces the effect of efficiently removing stagnant air in pulmonary alveoli or alveolar sacs (also referred to as alveolar parenchyma hereinafter) suffering from emphysema, or alleviating or preventing the overexpansion of the lung which weakens a patient due to emphysema or occlusion of air-supply bronchi to maintain the reduced volume by respiration. It also produces the effect of restoring the alveolar parenchyma suffering from emphysema to its original size or less, thereby suppressing or preventing the compression or occlusion of the surrounding bronchi by the surrounding alveolar parenchyma. The method for treatment according to the present invention employs a catheter and does not need any surgical treatment, and this imposes a less burden to a patient. In addition to the foregoing, the present invention produces the effect of forming a film on the inner wall of alveolar parenchyma suffering from emphysema, thereby alleviating and preventing the overexpansion of the lung to restore the elasticity of the alveolar parenchyma suffering from emphysema.

Generally, the normal lung has no bypass or a very small bypass between adjacent alveoli; however, alveolar parenchyma suffering from emphysema often has holes called bypass that connect neighboring pulmonary alveoli to one another. This bypass permits air to enter when an attempt is made to suck out air by inserting a catheter into the overexpanded alveolar parenchyma suffering from emphysema, and such an attempt fails to alleviate the overexpansion of the lung. According to the present invention, this difficulty is overcome by injecting a film-forming agent into the respiratory region including the pulmonary alveoli or alveolar sacs, thereby forming a film on the inner wall of the respiratory region and substantially closing the alveolar parenchyma suffering from emphysema. The result is that no or little air leaks when air is sucked out from the alveolar parenchyma suffering from emphysema, and hence air in the closed system is removed completely and the volume of the alveolar parenchyma decreases readily, efficiently, and rapidly.

The invention will be described below in more detail with reference to the accompanying drawings.

Figure 1A:
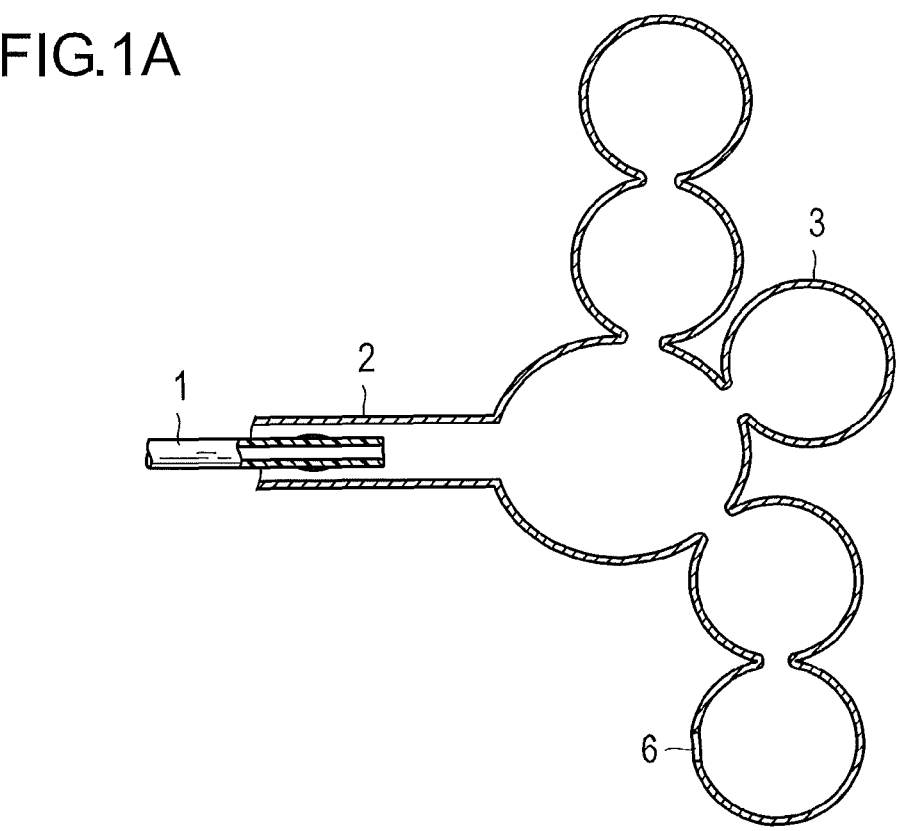
FIGS. 1A to 1C are schematic sectional views showing the sequential steps of the method according to the present invention.
Figure 1B:
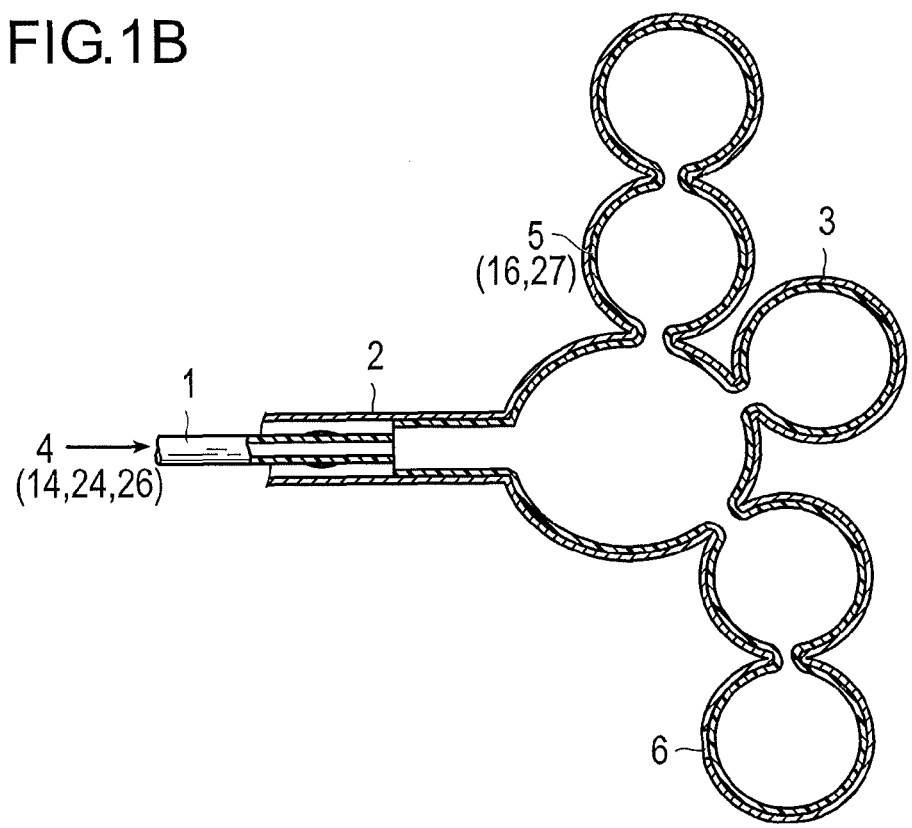
Figure 1C:
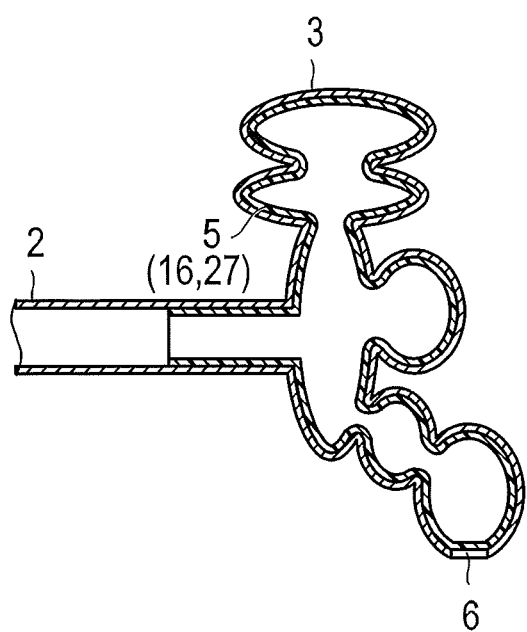

FIGS. 1A to 1C are schematic sectional views showing the sequential steps of the method according to the present invention. The method according to the present invention comprises inserting the catheter 1 into the bronchus or bronchiole 2 [step (a)], injecting through said catheter the film-forming agent 4 (14, 24, 6) into the respiratory region including the pulmonary alveoli or alveolar sacs 3, thereby forming the film 5 (16, 27) on the inner wall of said respiratory region [step (b)], and shrinking said pulmonary alveoli or alveolar sacs [step (c)] as shown in FIG. 1A. Each step will be described below in more detail, but it is not limited to the following.

1. Step (a)

This step is intended to insert the catheter into the bronchus or bronchiole. To be more specific, this step is intended to insert the catheter 1 into the bronchus or bronchiole 2 communicating with the respiratory region including the pulmonary alveoli or alveolar sacs suffering from emphysema (referred to as alveolar parenchyma suffering from emphysema hereinafter) 3 as shown in FIGS. 1A, 2A, 3A and 4A.

The catheter used in this step is not specifically restricted; it will be properly selected according to the diameter (or the number of branching) of the bronchus or bronchiole into which it is introduced. To be concrete, it may be selected from any known medical catheters for the respiratory system, circulatory system, and digestive system. The catheter is not specifically restricted in structure, and it may or may not have a balloon. The one with a balloon is desirable because of ease with which it is inserted into the tract or its sealing ability. Also, the catheter is not restricted in the number of its lumens. The number of lumens should be properly selected according to the number of agents to be used in the steps (b) and (c), which will be described below in more detail, and the presence or absence of the balloon.

Figure 5A:
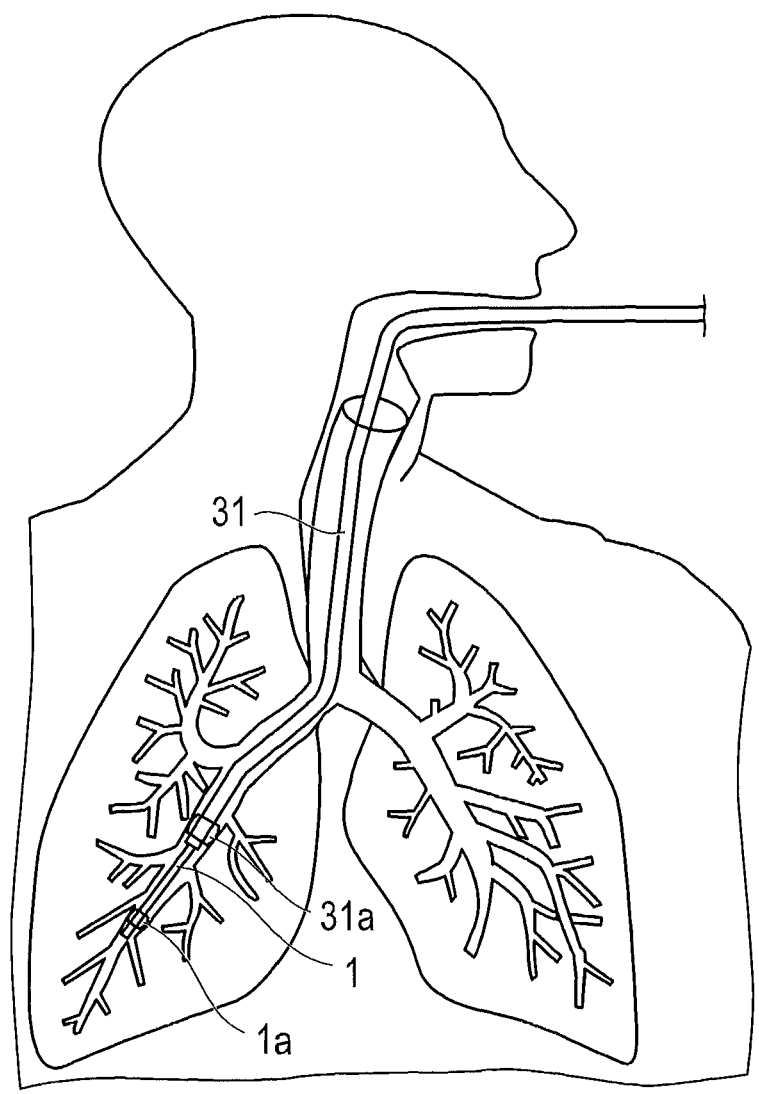
FIGS. 5A and 5B are schematic sectional views showing the step (a) according to the preferred embodiment of the present invention.

The insertion of the catheter 1 into the alveolar parenchyma 3 suffering from emphysema will be facilitated with the help of the sheath 31 extending to the desired position, as shown in FIG. 5A. The sheath 31 is not specifically restricted in structure, and it may or may not have a balloon. However, it should preferably have the balloon 31*a* which can close the bronchus or bronchiole. The balloon 31*a* attached to the sheath 31 and the balloon 1*a* attached to the catheter 1 may be placed at any position in the bronchus or bronchiole without specific restrictions. The balloon 31*a* attached to the sheath 31 should preferably be placed in the bronchus, and the balloon 1*a* attached to the catheter 1 should preferably be placed near the terminal of the bronchus, particularly in the bronchiole. The closing of the bronchus or bronchiole with the balloon 31a heightens the air tightness at the part away from the sheath. This leads to the effective use of the catheter for the treatment of alveolar parenchyma suffering from emphysema. In addition, the balloon 1a and the balloon 31a may be used to close different positions in the bronchus or bronchiole. In this way it is possible to easily and separately control the pressure in the space between the balloon 1a and the balloon 31a (for example, the normal alveolar parenchyma) and the pressure at the periphery of the balloon 1a (for example, the alveolar parenchyma suffering from emphysema).

With the bronchus or bronchiole closed by the balloon 31a, the space on the proximal side of the balloon 31a is given an adequate breathing pressure necessary for pulmonary ventilation and this permits efficient and safe treatment. Expansion and shrinkage of the balloon 31a may be accomplished in any way without specific restrictions; the most convenient way is by means of the three-way stopcock 34 attached to the base end of the sheath 31.

Figure 5B:
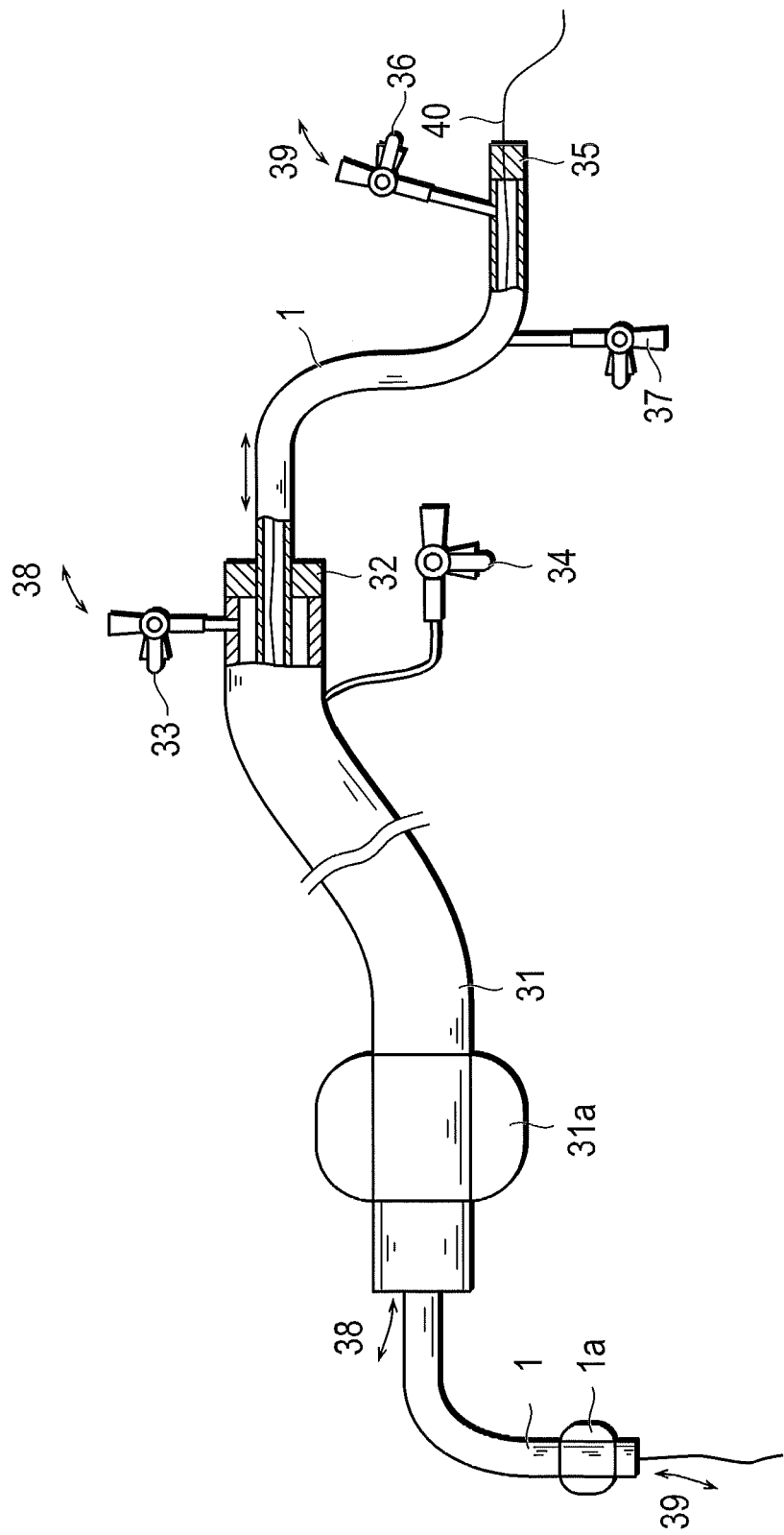

The balloon 31a attached to the sheath 31 keeps constant the pressure in the space beyond it, and this permits stable operation at the forward end of the catheter 1. For example, when the bronchus or bronchiole is closed by the balloon 31a and the space beyond the sheath 31 is decompressed, the wall of the bronchus or bronchiole tightly adheres to the balloon 1a attached to the catheter 1. Thus the balloon 1a prevents air from flowing through the bypass into the space beyond the catheter 1, thereby facilitating decompression in the space beyond the catheter. This also produces the effect of keeping the pressure in the space beyond the sheath 31 constantly lower than the pressure for drug injection when a drug is being injected at a constant pressure into the space beyond the catheter 1. The result is an efficient drug delivery. No specific restrictions are imposed on the way of controlling the pressure at the forward end (periphery) of the sheath 31 or at the forward end (periphery) of catheter 1. One typical method for pressure control is shown in FIG. 5B. The sheath 31 is provided with the sealing stopcock 32 at its base end, so that the catheter 1 is inserted into the sheath 31 through the sealing stopcock 32. This arrangement closes the alveolar parenchyma beyond the forward end (periphery) of the sheath 31 and permits easy pressure control in that part. The sheath 31 is also provided at its base end with the three-way stopcock 33 through which the gas 38 is introduced or sucked in order to control the pressure in the alveolar parenchyma beyond the forward end (periphery) thereof. The same way as mentioned above is used to control the pressure at the forward end (periphery) of the catheter 1. That is, as shown in FIG. 5B the catheter 1 is provided with the sealing stopcock 35 at its base end. This arrangement closes the alveolar parenchyma beyond the forward end (periphery) of the catheter 1 and permits easy pressure control in that part. The catheter 1 is also provided at its base end with the three-way stopcock 36 through which the gas or liquid 39 is introduced or sucked in order to control the pressure in the alveolar parenchyma beyond the forward end (periphery) thereof. No specific restrictions are imposed on the way of expanding or shrinking the balloon 1a. One typical way is by using the three-way stopcock 37 attached to the base end of the catheter 1. In addition, the catheter 1 may have a lumen as a passage for the guide wire 40 which helps insertion of the catheter 1 to the desired position.

For example, the catheter 1 may be one which is provided with the balloon 1a to close the bronchus. (This catheter has a lumen to deliver a liquid through the openings close to and away from the desired part.) The catheter 1 may also be a PTCA catheter of OTW type which is used for treatment of angiostenosis in the cardiovascular region. The catheters mentioned above may be commercial ones include microcatheter (such as FINECROSS (registered trademark), made by TERUMO CORPORATION), which is intended to pass a guide wire through angiostensis in the cardiovascular region, and PTCA catheter (such as Ryuj in Plus OTW (registered trademark), made by TERUMO CORPORATION). The foregoing catheter is so designed as to be inserted into the lumen of the bronchus through the working lumen of the bronchoscope; however, catheter does not necessarily need the bronchoscope so long as catheter can be arranged at any desired position. In addition, the catheter 1 or the balloon 1a may be expanded to any size in outside diameter without specific restrictions; an adequate size may be selected according to the diameter of the bronchus or bronchiole 2. Specifically, the outside diameter after expansion of the balloon 1a should preferably be slightly larger than the inside diameter of the bronchus or bronchiole 2 communicating with any alveolar sac (air saccule) or pulmonary alveoli tissue into which the catheter is inserted or which is to be covered. More desirably, the outside diameter (Y mm) after expansion of the balloon 1a should be about 1 to 2 times the inside diameter (X mm) of the bronchus or bronchiole 2. In this case, the catheter or balloon can be pressed against the bronchus or bronchiole which is formed from elastic smooth muscles without serious damages. In addition, the catheter or balloon also improves the removing efficiency of the film-forming agent 4 mentioned later in the case of being discharged from the respiratory region.

The catheter may be introduced into the bronchus or bronchiole 2, with a guide wire inserted into its lumen (for example, for liquid delivery) of the catheter. Operation in this manner permits the tip of the guide wire to be placed closer to the periphery than the tip of the catheter. In this way, it is possible to introduce the tip of the catheter to the tissue near the alveolar sac (air saccule) or pulmonary alveoli close to the periphery at the bronchus or bronchiole 2. The guide wire for this purpose will be selected from any known ones for medical treatment of the respiratory system, circulatory system, and digestive system. It may have an adequate outside diameter according to the size of the lumen of the catheter. An example of the guide wire (GW for short hereinafter) is Runthrough (registered trademark) (having an outside diameter of 0.014 inches made by TERUMO CORPORATION) which is used for treatment of the heart blood vessel.

The tip of the guide wire or catheter should preferably be provided with a radiopaque material, which indicates the position of the tip of the guide wire and catheter projecting from the forward end of the endoscope during X ray fluoroscopy. In this way the guide wire and catheter can be introduced to the respiratory region including the pulmonary alveoli or alveolar sac suffering from emphysema, which has previously located by X ray fluoroscopy or CT scanning. The guide wire is removed when X ray fluoroscopy reveals that the tip of the catheter has reached the desired position. The foregoing operation should preferably be carried out in such a way that the tip of the guide wire is positioned closer to the periphery than the tip of the catheter. In addition, the tip of the catheter should preferably have a reticulate or perforated structure so that it will not adhere to the inner wall of the respiratory region including pulmonary alveoli and alveolar sacs.

2. Step (b)

This step is intended to inject through the catheter the film-forming agent into the respiratory region including pulmonary alveoli or alveolar sacs, thereby forming a film on the inner wall of the respiratory region. Thus, even though there exist a bypass (indicated by the reference numeral 6 in FIG. 1A) in the alveolar parenchyma suffering from emphysema, the film-forming agent entirely covers the inner wall including the bypass of the alveolar parenchyma suffering from emphysema. As the result of this step, the alveolar parenchyma suffering from emphysema is closed except for openings communicating with the bronchi or bronchioles (see FIG. 1B). Thus, the closed alveolar parenchyma suffering from emphysema permits little or no air leakage when it is shrunk in the subsequent step. This ensures removal of air from the closed space and efficiently reduces the volume of the alveolar parenchyma. In addition, the film formed in this manner restores the elasticity of the alveolar parenchyma suffering from emphysema, thereby alleviating or preventing the overexpansion of the lung. Incidentally, the term "respiratory region" as used in this specification is a generic one that implies the respiratory organ at the periphery beyond the bronchus including the respiratory bronchiole and two alveoli. The respiratory region typically includes the bronchus, bronchiole, terminal bronchiole, respiratory bronchiole, alveolar duct, alveoli, alveolar sac, pulmonary veins, and pulmonary artery. It should preferably include the respiratory bronchiole, alveolar duct, alveoli, alveolar sac, and pulmonary veins.

The film-forming agent is injected through the catheter into the respiratory region including the alveoli or alveolar sacs, especially the alveolar parenchyma suffering from emphysema. This step should preferably be carried out by using the catheter 1 provided with the balloon 1a in such a way that the balloon 1a is expanded to close the bronchus or bronchiole 2 prior to injection of the film-forming agent 4, as shown in FIG. 2B. In other words, the method according to the present invention has the step (b) in which the bronchus or bronchiole is closed by expanding the balloon attached to the catheter before the film-forming agent is injected. This operation prevents the film-forming agent 4 from flowing backward toward the trachea (proximal side) from the bronchus or bronchiole 2 and permits the film-forming agent 4 to efficiently come into contact with the aimed alveolar parenchyma 3 suffering from emphysema. Expansion of the balloon 1a attached to the catheter 1 may be accomplished by any known method without specific restrictions. For example, this object may be achieved by using the syringe or indeflator connected to the lumen for balloon expansion arranged at the base end of the catheter. The balloon may be expanded by filling it with any material, such as air, contrast medium, and physiologic saline containing contrast medium, which is not specifically restricted. A gas, especially carbon dioxide or oxygen, is desirable in view of complication such as pneumonia. It is safe even in the case of leakage due to balloon damage. The balloon will be placed at any position unrestrictedly. For example, the balloon may be placed at the end of the catheter or at a position slightly close to the trachea (proximal side) and slightly away from the end of the catheter. In the case where the tip of the catheter is in the bronchus, the balloon should be attached to the catheter such that it does not go beyond the branch close to the bronchus.

According to a preferred procedure, the film-forming agent should be injected after air has been introduced into the respiratory region through the catheter. Since there exist usually no or very few bypasses in the normal alveolar parenchyma as mentioned above, the air injected into the respiratory region fills the normal alveolar parenchyma and hence the film-forming agent injected subsequently hardly enters the alveolar parenchyma. The normal alveolar parenchyma which accounts for a very small portion is affected negligibly by injection of the film-forming agent because there exist only a few bypasses. By contrast, since the alveolar parenchyma suffering from emphysema has small holes, called bypasses, communicating with neighboring pulmonary alveoli, the air injected into the respiratory region leaks through the bypasses and the film-forming agent which is injected subsequently easily enters the alveolar parenchyma suffering from emphysema. Consequently, the foregoing procedure permits the film-forming agent to be selectively injected into the alveolar parenchyma suffering from emphysema which has bypasses. The pressure for air injection is not specifically restricted so long as air does not substantially damage the normal alveolar parenchyma and the alveolar parenchyma suffering from emphysema and air sufficiently fills the normal alveolar parenchyma. That the normal alveolar parenchyma has been filled with air is known from the increased air injection pressure indicated by the pressure gauge at hand. Thus, air is injected according to the monitored air pressure, and if injection pressure rises, the speed of injection may be decreased or the injection may be suspended.

After air injection into the respiratory region through the catheter, the film-forming agent is injected at a pressure equal to or different from the air injection pressure. The injection pressure for the film-forming agent should preferably be substantially equal to the air injection pressure, so that the pressure in the normal alveolar parenchyma substantially balances with the injection pressure of the film-forming agent. In this situation there is no possibility of the film-forming agent entering the normal alveolar parenchyma or air escaping from the normal alveolar parenchyma. By contrast, upon injection, the film-forming agent enters the alveolar parenchyma suffering from emphysema selectively and efficiently because the air pressure in the alveolar parenchyma suffering from emphysema is lower than the injection pressure of the film-forming agent.

For this reason, it is desirable to inject air into the respirator region through the catheter and then inject the film-forming agent while keeping the same injection pressure.

During this operation, it is desirable to temporarily suspend the pulmonary ventilation and keep a constant pressure in the area surrounding the object in order that the lung in the area surrounding the object is not affected by pressure fluctuation. Such a constant pressure should preferably be lower than the pressure of air being injected through the catheter 1. For example, a desirable pressure may be a continued positive pressure or the open atmospheric pressure. The foregoing operation may be carried typically by closing the bronchus or bronchiole which is closer to the center than the aimed bronchus or bronchiole and then inserting the catheter 1 into the aimed bronchus or bronchiole while keeping the pressure constant. That part of the bronchus close to the center which is to be closed may be the central bronchus; however, it should preferably be the main bronchus or a part thereof close to the periphery side so that the remaining parts can continue ventilation. Particularly, as shown in FIG. 5A, the sheath 31 is arranged at a closer position than the catheter 1 to be inserted into the alveolar parenchyma 3 suffering from emphysema. The pressure (Pressure 1) in the bronchus and bronchiole between the balloon 1a and the balloon 31a (for example, the normal alveolar parenchyma) can be kept lower than the pressure (Pressure 2) of injection through the catheter 1 (Pressure 1<Pressure 2). The former pressure should preferably be a positive pressure or the open atmospheric pressure. On the other hand, closing the balloon 1a attached to the catheter 1 prevents the film-forming agent 4 from flowing backward into the trachea (proximal side) of the bronchus or bronchiole 2. This permits the film-forming agent 4 to efficiently come into contact with the aimed alveolar parenchyma 3 suffering from emphysema. Any method may be used unrestrictedly to control the pressure (Pressure 1) in the bronchus and bronchiole between the balloon 1a and the balloon 31a (for example, the normal alveolar parenchyma) and the pressure (Pressure 2) for injection through the catheter 1. According to a preferred example of the method as shown in FIG. 5B, the sheath 31 is provided with the sealing stopcock 32 at the base end thereof and the catheter 1 is inserted into the sheath 31 through the sealing stopcock 32. The sealing stopcock 32 closes the alveolar parenchyma beyond the tip (periphery) side of the sheath 31, and this permits an easy control of pressure in that part. In addition, the sheath 31 is provided with the three-way stopcock 33 at its base end. This three-way stopcock 33 permits the gas 38 to be introduced or discharged so that the pressure (Pressure 1) in the bronchus and bronchiole (for example, the normal alveolar parenchyma) between the balloon 1a and the balloon 31a can be controlled positive or at the open atmospheric pressure. The foregoing is also applied to control the pressure of injection through the catheter 1. That is, the catheter 1 is provided with the sealing stopcock 35 at its base end as shown in FIG. 5B. The sealing stopcock 35 permits the gas to fill selectively and easily the closed normal alveolar parenchyma. The catheter 1 may be provided with the three-way stopcock 36 at its base end, which helps to control the pressure (Pressure 2) of injection through the catheter 1 by introducing or discharging the gas 39 through the three-way stopcock 36.

This step is intended to form film on the inner wall of the respirator region by injection of the film-forming agent into the respirator region including the pulmonary alveoli or alveolar sacs. This object may be achieved by any method, without specific restrictions, such as (b-1) to (b-3), illustrated in the following.

(b-1): This method comprises injecting a solution of viscous polymer as the film-forming agent into the respiratory region through the catheter and then removing by suction an excess of the solution of viscous polymer;

(b-2): This method comprises injecting the film-forming agent (which is a material that cures upon reaction with water or divalent metal ions) into the respiratory region through the catheter and then removing by suction the material after reaction with water or divalent metal ions present on the surface of the respiratory region; or (b-3): This method comprises injecting a polymeric electrolyte (A) into the respiratory region through the catheter, removing by suction an excess of the polymeric electrolyte (A), thereby allowing the polymeric electrolyte (A) to form a film on the inner wall of the respiratory region, injecting a polymeric electrolyte (B) which is charged opposite to the polymeric electrolyte (A) into the respiratory region through the catheter, thereby allowing the polymeric electrolyte (B) to come into contact with the polymeric electrolyte (A), and removing by suction an excess of the polymeric electrolyte (B). This method may optionally has an additional step of injecting the polymeric electrolyte (A) into the respiratory region through the catheter after removal of the polymeric electrolyte (B) by suction, and removing by suction an excess of the polymeric electrolyte (A) (in this case, the polymeric electrolyte (A) and the polymeric electrolyte (B) serve as the film-forming agent).

The preferable methods (b-1) to (b-3) are described below in more detail; however, the following does not aim to restrict the scope of the present invention.

2-1. Step (b-1)

Figure 2A:
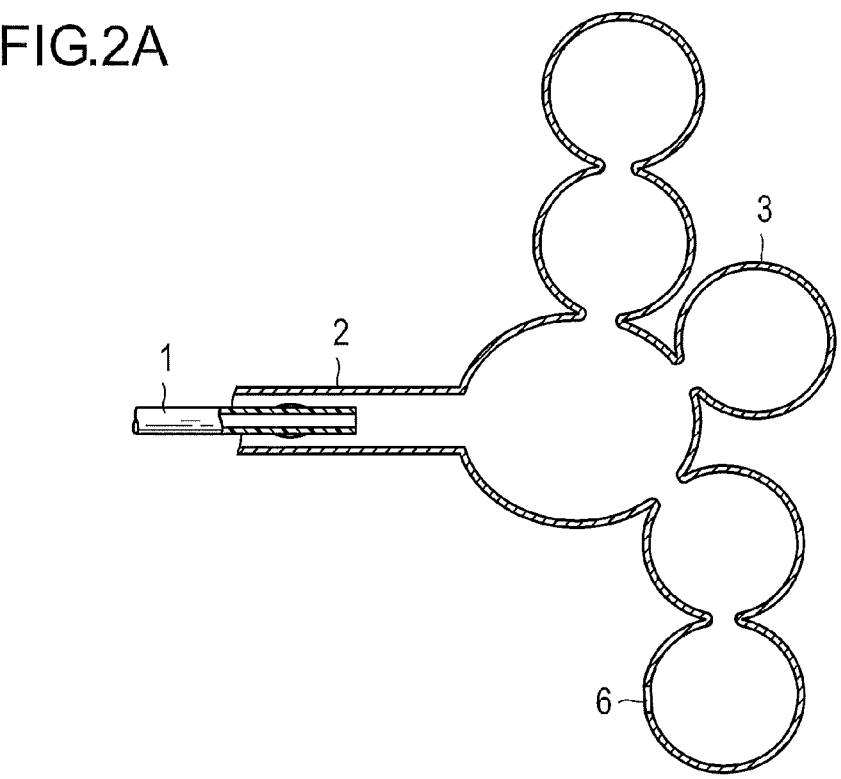
FIGS. 2A to 2F are schematic sectional views showing the sequential steps of the preferred method according to the first embodiment of the present invention.
Figure 2B:
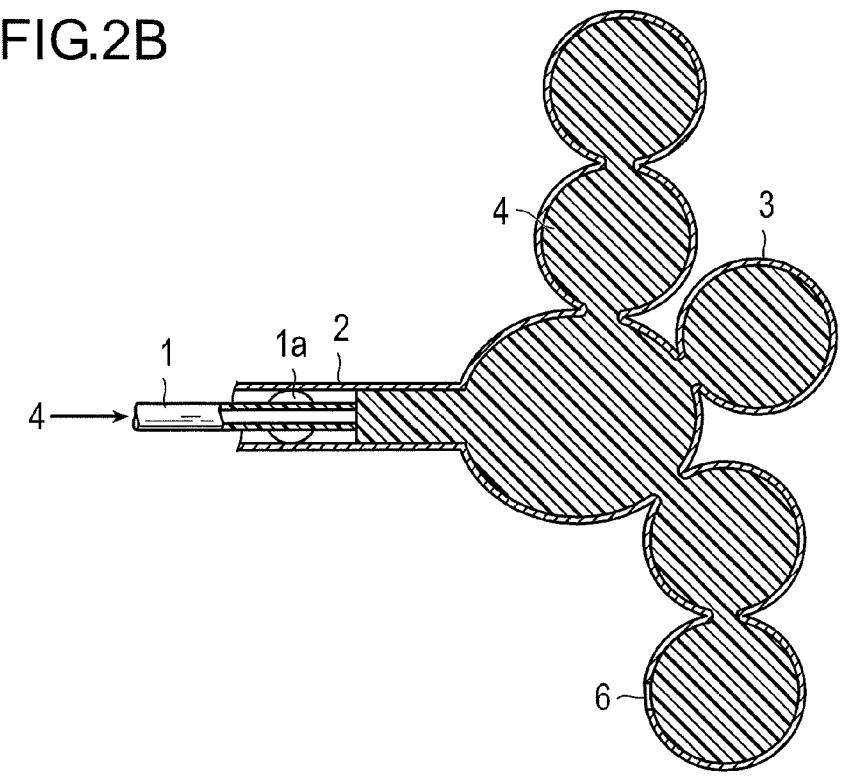
Figure 2C:
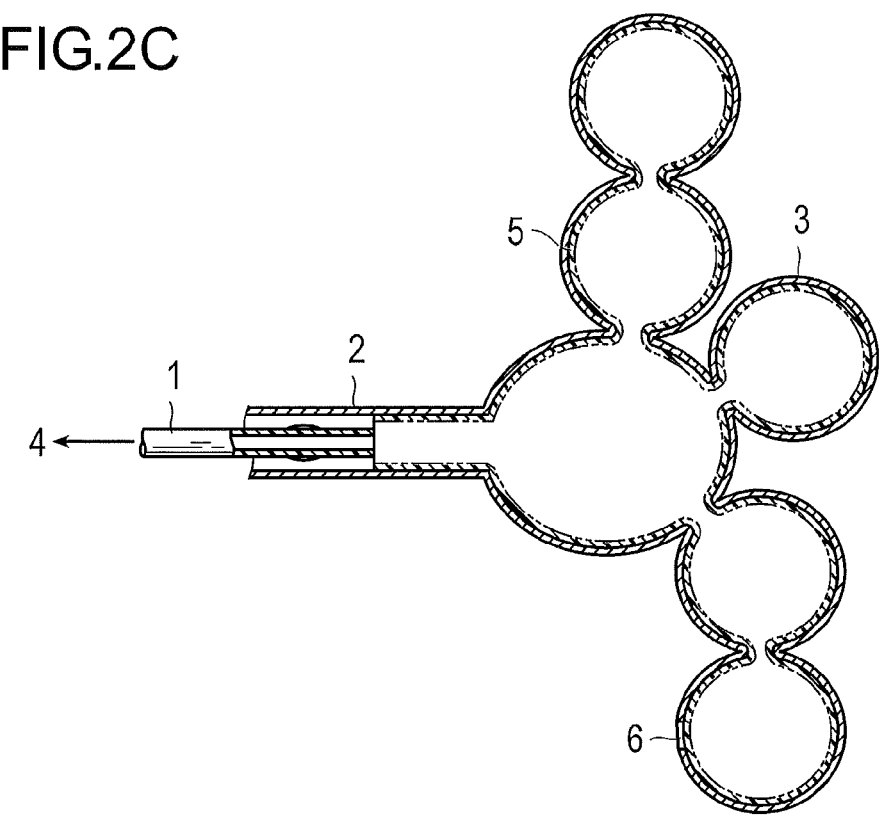

This step, shown in FIGS. 2B and 2C, involves injecting through the catheter 1 the solution of viscous polymer 4 as the film-forming agent into the bronchus or bronchiole 2 and into the respiratory region including the alveoli or alveolar sacs 3 (as shown in FIG. 2B) and then removing by suction an excess of the solution of viscous polymer 4 (as shown in FIG. 2C). Incidentally, at the time of injection of the solution of viscous polymer or removal of an excess of the solution of viscous polymer by suction, it is desirable to expand the balloon 1a so as to seal the space between the catheter 1 and the bronchus or bronchiole 2. Sealing in this manner permits secure injection of the solution of viscous polymer and secure removal of an excess of the solution of viscous polymer by suction.

The solution of viscous polymer 4 mentioned above forms, on account of its viscous property, a thin film 5 of the solution on the inner wall of the respiratory region 3 (or the alveolar parenchyma suffering from emphysema in the illustrated case) after removal by suction of the solution. In addition, the thus formed film 5 covers the bypass 6, even if the bypass 6 might exist in the alveolar parenchyma 3 suffering from emphysema, because the bypass is usually a small hole. As a result, the alveolar parenchyma 3 suffering from emphysema is closed except for the holes communicating with the bronchus (FIG. 2C). The foregoing step of shrinking the alveolar parenchyma suffering from emphysema permits the alveolar parenchyma suffering from emphysema to shrink readily and efficiently in the subsequent step because there is no air leakage through the bypass 6.

Incidentally, the solution of viscous polymer 4 may be optionally injected and removed by suction repeatedly, so that the inner wall of the alveolar parenchyma suffering from emphysema is coated entirely and firmly with the film 5. The resulting film securely restores elasticity of the alveolar parenchyma suffering from emphysema, thereby alleviating and preventing more the overexpansion of the lung. Also, if the bypass exists, the film securely closes the bypass. Moreover, it is possible to easily control the film thickness by repeating the above-mentioned step. Further, it is possible to inject air after an excess of the solution has been removed by suction, optionally. Air injection in this manner smoothens the inner wall of the alveolar parenchyma suffering from emphysema, thereby improving adhesion between the film and the inner wall, even in the case where suction to remove an excess of the solution shrinks the alveolar parenchyma suffering from emphysema and roughens its inner wall, thereby deteriorating adhesion between the film and the inner wall.

The viscous polymer mentioned above denotes any polymer which exhibits viscosity (adhesiveness) when applied to a tissue of living body, such as the alveolar parenchyma. The viscous polymer is not specifically restricted so long as the viscous polymer sticks to the alveolar parenchyma and closes the bypass. The viscous polymer is selected from the following materials which are commonly used for medical treatment. In particular, there are provided starch, gum arabic, sodium alginate, propylene glycol alginate, carboxyvinyl polymer, carmellose sodium, xanthan gum, gellan gum, gelatin, hydrolyzed gelatin, polyacrylic acid, polyacrylate, partially neutralized polyacrylate, starch polyacrylate, polyvinylpyrrolidone, hydroxyethyl cellulose, hydroxypropyl cellulose, hydroxypropyl methyl cellulose, polyvinyl alcohol (PVA), methyl cellulose (MC), carboxymethyl cellulose (CMC), carboxymethyl cellulose sodium, and the like. The above-mentioned viscous polymers may be used alone or in combination with one another. Preferable among the forgoing viscous polymer are water-soluble polymers such as carboxyvinyl polymer, hydroxyethyl cellulose, hydroxypropyl cellulose, hydroxypropyl methyl cellulose, polyvinyl alcohol, methyl cellulose, starch, sodium alginate, gelatin, and hydrolyzed gelatin. More preferable examples include starch, sodium alginate, gelatin, and hydrolyzed gelatin. They readily adhere (stick) to the tissue of the living body and hardly run down from the applied part. The film formed from these materials is highly integral with the alveolar parenchyma suffering from emphysema and hence hardly peels off after the alveolar parenchyma is shrunk in the subsequent step.

The solution of viscous polymer may be prepared by using any solvent listed below which can dissolve or disperse the viscous polymer. Examples are water; dimethylsulfoxide, dimethylformamide; glycols such as ethylene glycol, diethylene glycol, propylene glycol, triethylene glycol, polyethylene glycol, and polypropylene glycol; and oils and fats such as olive oil, castor oil, squalane, and lanolin. The foregoing solvents may be used alone or in combination with one another. Of these examples, water and dimethylsulfoxide are preferable, and water is more desirable. They are excellent in safety.

The solution of viscous polymer may contain the viscous polymer in any concentration unrestrictedly; however, preferable concentrations are 0.5 to 50 wt %. These concentrations are suitable for the solution of viscous polymer to adequately adhere (stick) to the inner wall of the alveolar parenchyma.

The amount of the solution of viscous polymer to be introduced into the alveolar parenchyma suffering from emphysema is not specifically restricted so long as it is enough for the solution of viscous polymer to fill the alveolar parenchyma suffering from emphysema. For example, injection should be suspended when an increase in the injection pressure of the solution of viscous polymer is detected. Likewise, the amount of an excess of the solution of viscous polymer to be removed by suction after introduction is not specifically restricted so long as the amount is substantially enough for removal from the alveolar parenchyma suffering from emphysema. Removal by suction should be suspended when the solution of viscous polymer cannot be sucked. Incidentally, the solution of viscous polymer may be introduced and removed through either the same lumen or the different lumens of the catheter, but using the same lumen is desirable for easy operation.

The solution of viscous polymer which has been applied to the inner wall of the alveolar parenchyma suffering from emphysema may be held there for an unrestricted period of time; however, duration of one to five minutes is desirable for the solution of viscous polymer to start curing and forming the film on the inner wall of the alveolar parenchyma suffering from emphysema.

As mentioned above, the inside of the alveolar parenchyma suffering from emphysema is substantially closed except for openings communicating with the bronchus or bronchiole. Therefore, the solution of viscous polymer as the film-forming agent is somewhat integral with the lumen of the alveolar parenchyma 3 suffering from emphysema when the solution of viscous polymer is removed by suction. Hence, the alveolar parenchyma 3 shrinks as the removal by suction proceeds.

2-2. Step (b-2)

Figure 3A:
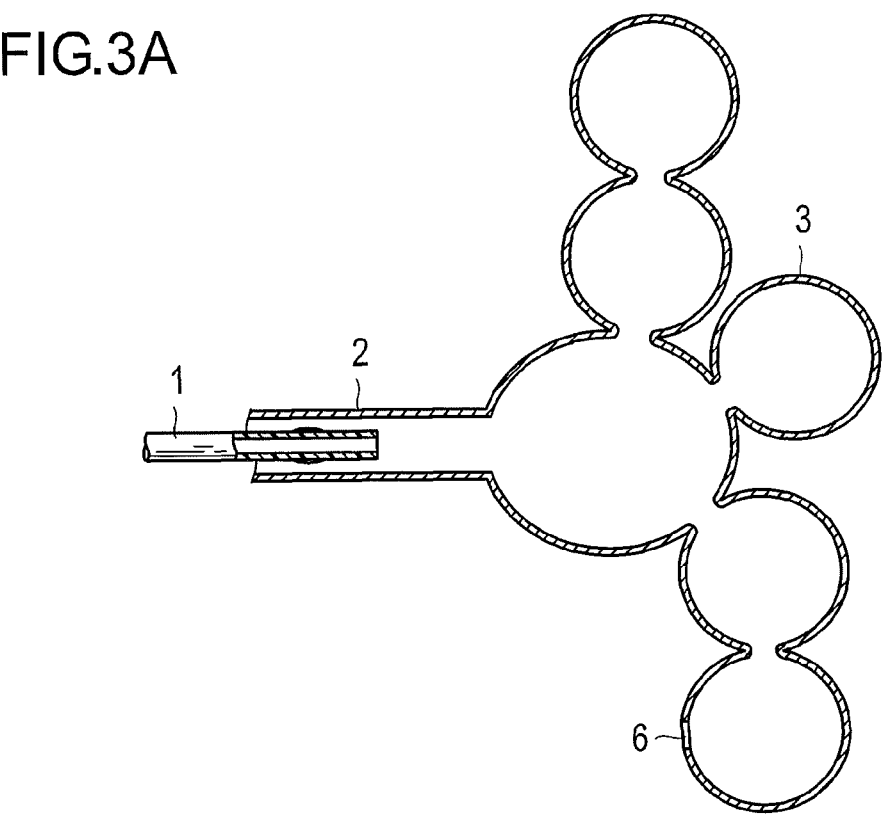
FIGS. 3A to 3E are schematic sectional views showing the sequential steps of the preferred method according to the second embodiment of the present invention.
Figure 3B:
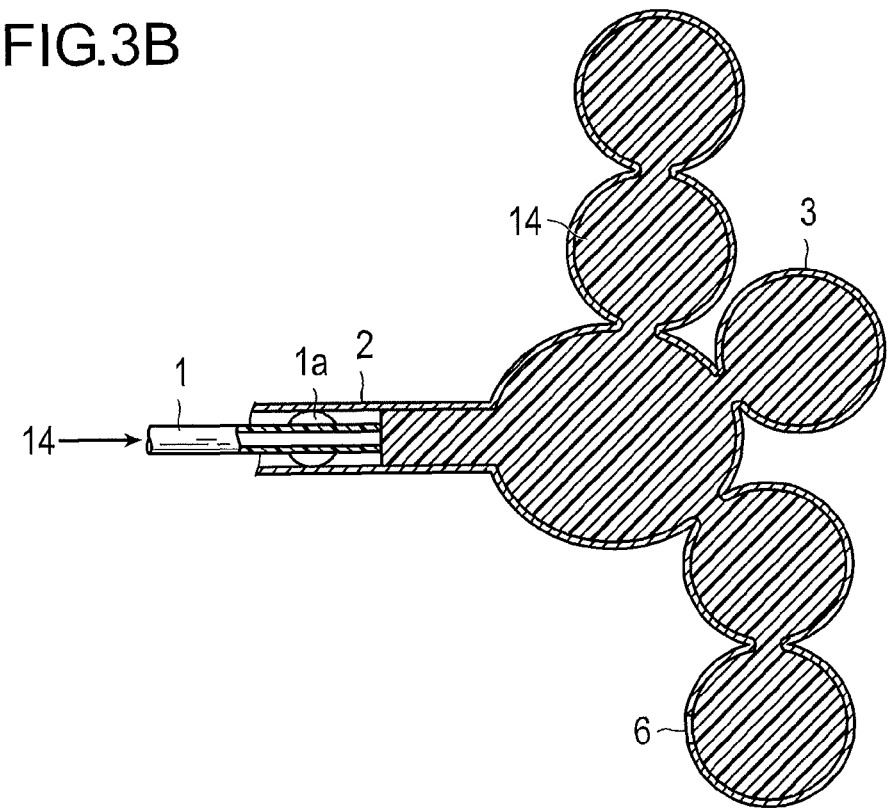
Figure 3C:
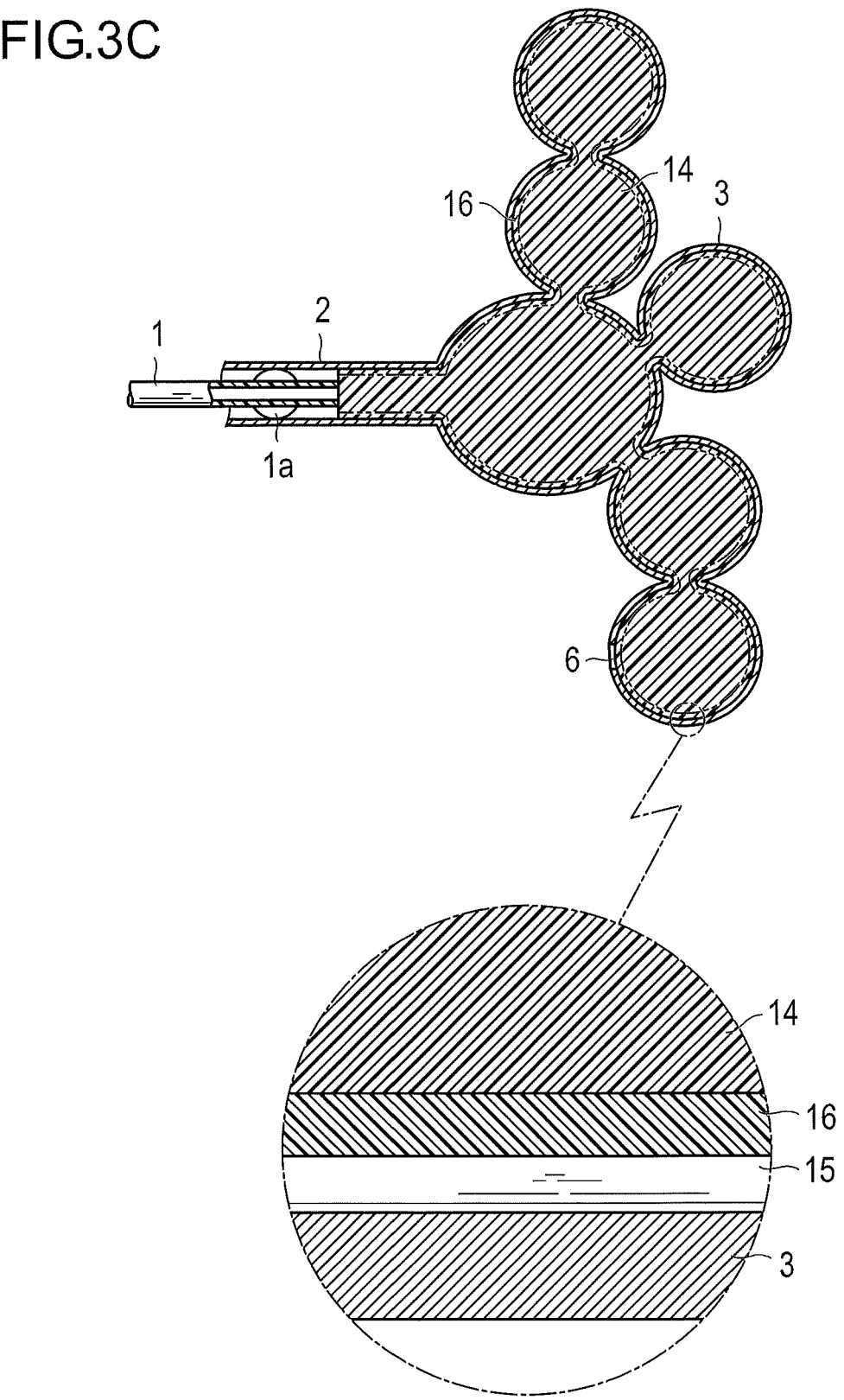
Figure 3D:
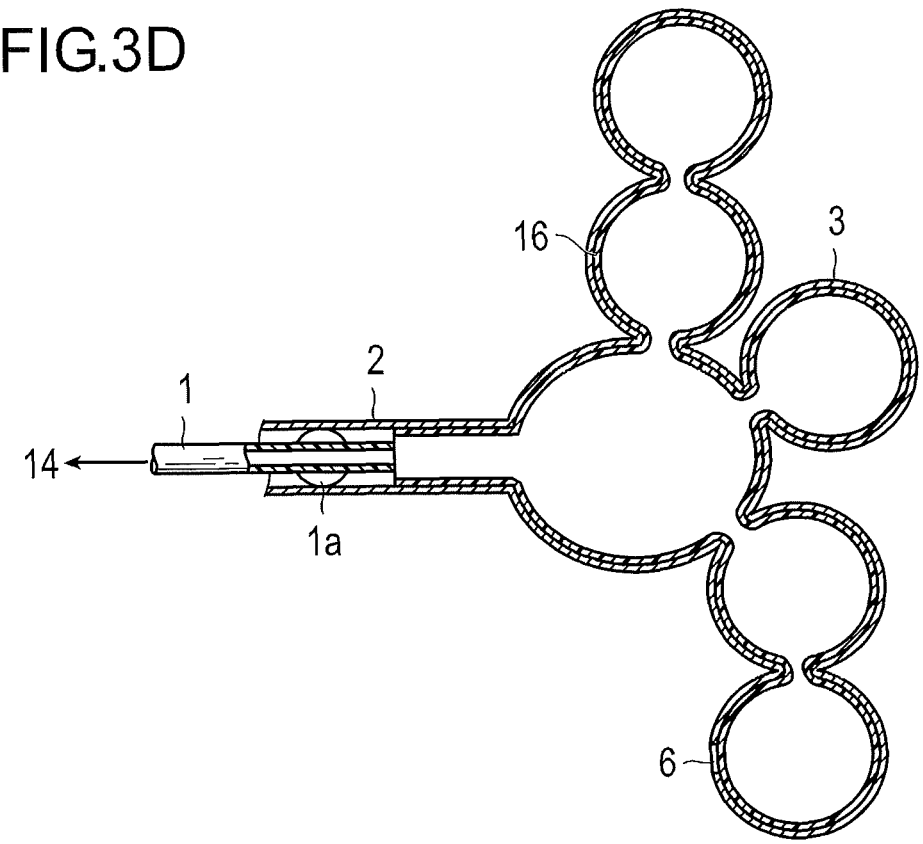

This step, shown in FIGS. 3B and 3C, involves injecting through the catheter 1 the film-forming agent, which is the material 14 capable of curing upon reaction with water or divalent metal ions, into the respiratory region 2 (FIG. 3B) and then allowing the material 14 to react with water or divalent metal ions (such as calcium ions) 15 present on the inner wall of the respiratory region (which is the alveolar parenchyma suffering from emphysema in the figures) 3. Incidentally, when the material 14 is injected, it is desirable to expand the balloon 1a and seal the gap between the catheter 1 and the inner wall of the bronchus or bronchiole 2 (FIG. 3C). In this way the material 14 can be securely injected into the respiratory region (which is the alveolar parenchyma suffering from emphysema in the figures) 3 without the material 14 flowing backward. The above-mentioned reaction cures the material 14 to form the film 16 on the surface of the alveolar parenchyma 3 suffering from emphysema (FIG. 3C). Incidentally, that portion of the material 14 which does not come into contact with water or divalent metal ions 15 present on the surface of the alveolar parenchyma 3 suffering from emphysema remains as such without reaction (curing) (see the enlarged part of FIG. 3C). The unreacted (uncured) portion of the material 14 is rapidly removed by suction in the subsequent step (c), with the film 16 remaining (FIG. 3D). Incidentally, when the material 14 is removed by suction, it is desirable to expand the balloon 1a so as to seal the gap between the catheter 1 and the inner wall of the bronchus or bronchiole 2. In this way, it is possible to securely remove the material 14 from the alveolar parenchyma 3 suffering from emphysema without the material 14 flowing toward the bronchus. In addition, the film 16 is formed so as to cover the bypass 6, even if the bypass 6 exists in the alveolar parenchyma 3 suffering from emphysema, because the bypass is usually a small hole. As the result of the foregoing step, the alveolar parenchyma 3 suffering from emphysema is closed except for the holes communicating with the bronchus (FIG. 3D). The foregoing step permits the alveolar parenchyma suffering from emphysema to shrink readily and efficiently in the subsequent step of shrinking the alveolar parenchyma suffering from emphysema because there is no air leakage through the bypass 6.

The material 14 capable of curing upon reaction with water, which is used as the film-forming material, is not specifically restricted so long as the material 14 starts to react (cure) with water on the surface of the tissue such as alveolar parenchyma of the living body and the material 14 also closes bypasses which might exist. Its preferable examples include various kinds of cyanoacrylate monomer as listed below, which form polycyanoacrylate upon reaction with water. In particular, the examples are Alkyl- and cycloalkyl-α-cyanoacrylate, such as methyl-α-cyanoacrylate, ethyl-α-cyanoacrylate, propyl-α-cyanoacrylate, butyl-α-cyanoacrylate, cyclohexyl-α-cyanoacrylate, heptyl-α-cyanoacrylate, and octyl-α-cyanoacrylate; alkenyl- and cycloalkenyl-α-cyanoacrylate, such as allyl-α-cyanoacrylate, methallyl-α-cyanoacrylate, and cyclohexenyl-α-cyanoacrylate; alkynyl-α-cyanoacrylate, such as propargyl-α-cyanoacrylate; aryl-α-cyanoacrylate, such as phenyl-α-cyanoacrylate and toluoyl-α-cyanoacrylate; hetero-atom-containing methoxyethyl-α-cyanoacrylate, ethoxyethyl-α-cyanoacrylate, and furfuryl-α-cyanoacrylate; and silicon-containing trimethylsilylmethyl-α-cyanoacrylate, trimethylsilylethyl-α-cyanoacrylate, trimethylsilylpropyl-α-cyanoacrylate, and dimethylvinylsilylmethyl-α-cyanoacrylate. The foregoing α-cyanoacrylate compounds may be used alone or in combination with one another. Preferable among these examples are cyclohexyl-α-cyanoacrylate, heptyl-α-cyanoacrylate, and octyl-α-cyanoacrylate. Because of the long ester side chain of cyanoacrylate, the cyanoacrylate give rise to a soft polymerized product (cured layer) which permits the alveolar parenchyma (alveoli or alveolar sacs) suffering from emphysema to readily shrink in the subsequent step (c).

The material 14 capable of curing upon reaction with water, which serves as the film-forming material, may contain a plasticizer in addition to the cyanoacrylate monomer. The plasticizer makes the resulting film flexible so that the alveolar parenchyma (alveoli or alveolar sacs) suffering from emphysema readily shrink in the subsequent step (c).

The material 14 capable of curing upon reaction with divalent metal ions, which serves as the film-forming material, will form the film by reaction (for curing) with calcium ions present on the surface of the alveolar parenchyma suffering from emphysema. Or, injection of the material 14 may be preceded by injection of a solution containing divalent metal ions into the respiratory region 2 through the catheter 1. This additional step promotes film formation. The solution containing divalent metal ions is not specifically restricted so long as it is capable of reacting with the material 14 and closing the bypass which might exist. It should be properly selected according to the kind of the material 14. A typical example of the combination of the material 14 and the solution containing divalent metal ions is a combination of alginic acid and a compound which yields divalent ions, such as calcium ions, magnesium ions, and barium ions in an aqueous solution. Such a compound includes, for example, calcium chloride, calcium hydrogen phosphate, calcium dihydrogen phosphate, calcium triphosphate, calcium sulfate, calcium hydroxide, magnesium chloride, and barium chloride. An aqueous solution of alginic acid and a compound that forms calcium ions in the solution are preferable. In this case, the alginic acid undergoes crosslinking reaction with the calcium compound, thereby forming a gel which efficiently forms a film on the inner wall of the alveolar parenchyma suffering from emphysema. Incidentally, the solution containing divalent metal ions is injected and removed by suction in the same way as the material 14.

The material 14 capable of curing by reaction with water or divalent metal ions, which serves as the film-forming agent, may be introduced into the alveolar parenchyma suffering from emphysema in any unrestricted amount which is enough to fill the alveolar parenchyma suffering from emphysema. For example, injection of the material 14 should be suspended as soon as an increase in injection pressure of the material 14 is detected.

The material 14 may be kept in contact with water in the alveolar parenchyma suffering from emphysema or divalent metal ions (for example, calcium ion) for any unrestricted period of time, preferably one to five minutes. This duration is enough for the material 14 to react completely with water in the alveolar parenchyma suffering from emphysema or divalent metal ions. It is desirable to previously observe how the reaction proceeds when the film-forming agent 14 is dropped onto a slide glass at the same time of operation in the living body and then water is dropped onto the film-forming agent 14. The water droplets simulate water present on the surface of the alveolar parenchyma suffering from emphysema or divalent metal ions 15. The foregoing procedure reveals the reaction between the film-forming agent 14 and water or divalent metal ions 15 that proceeds in the living body. It also easily and accurately provides reaction state necessary to easily control the length of time for the film-forming agent to be in contact with the inner wall of the alveolar parenchyma. Even though there exist the bypass 6 in the alveolar parenchyma suffering from emphysema, the film-forming agent 14 forms the film 16 upon contact with water present on the surface of the alveolar parenchyma suffering from emphysema or with divalent metal ions 15, thereby closing the bypass 6. With the bypass 6 closed, it is possible to efficiently remove by suction the film-forming agent 14 which remains unreacted.

As mentioned above, the inside of the alveolar parenchyma suffering from emphysema is substantially closed except for openings communicating with the bronchus or bronchiole. Therefore, the film-forming agent 14 is somewhat integral with the lumen of the alveolar parenchyma 3 suffering from emphysema when the film-forming agent 14 is removed, and hence the alveolar parenchyma 3 shrinks as the removal by suction proceeds.

2-3. Step (b-3)

Figure 4A:
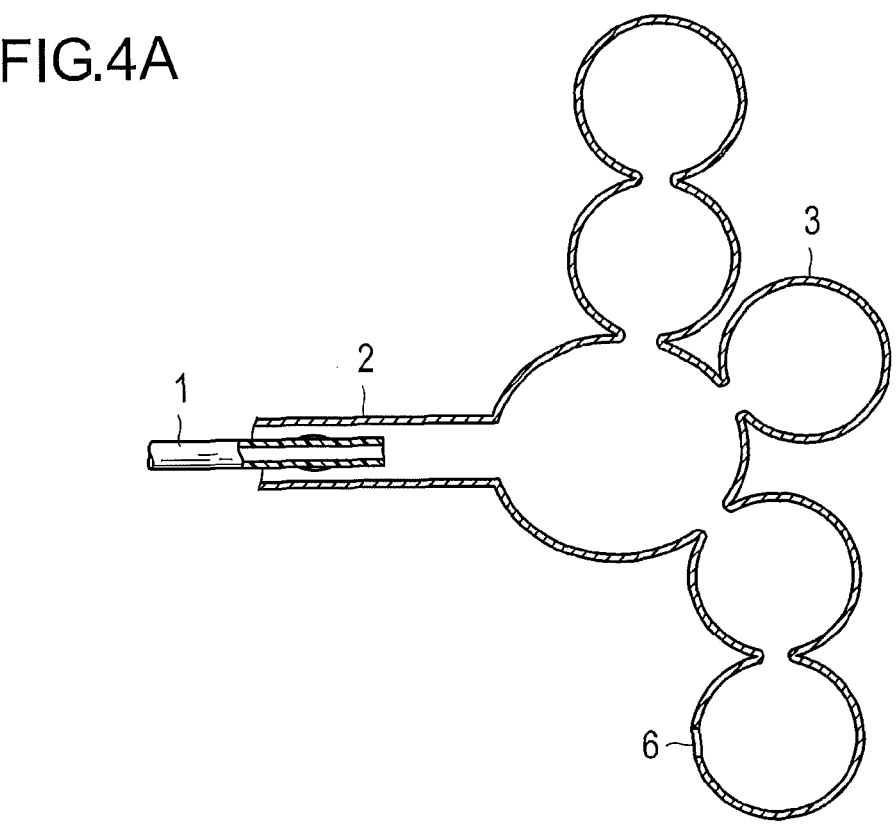
FIGS. 4A to 4F are schematic sectional views showing the sequential steps of the preferred method according to the third embodiment of the present invention.
Figure 4B:
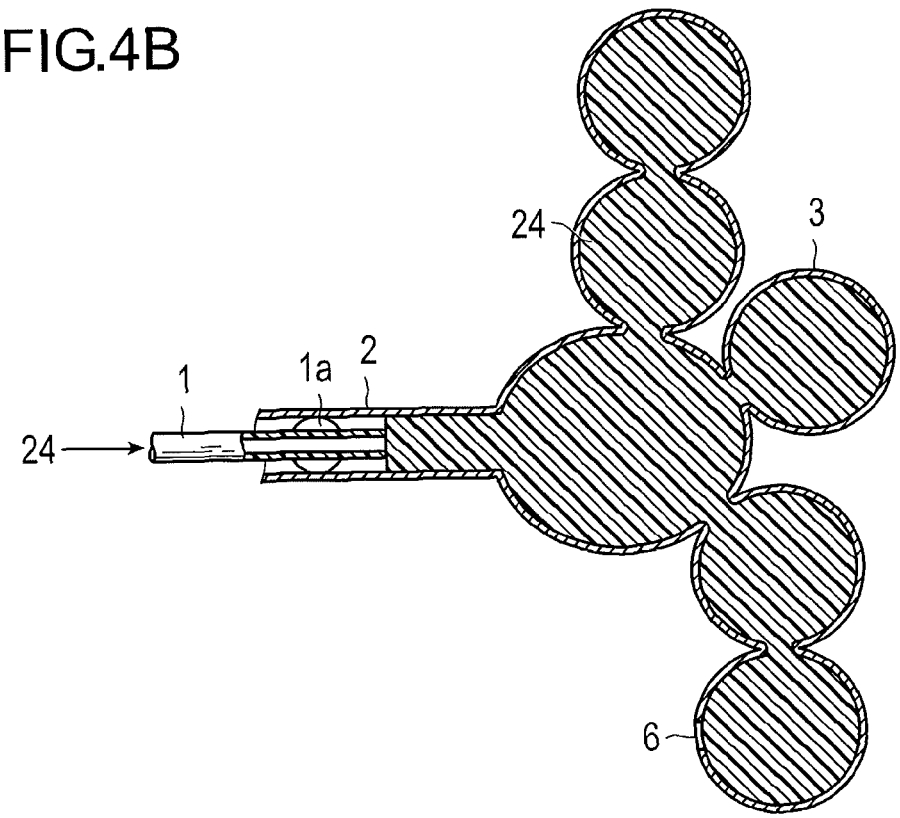
Figure 4C:
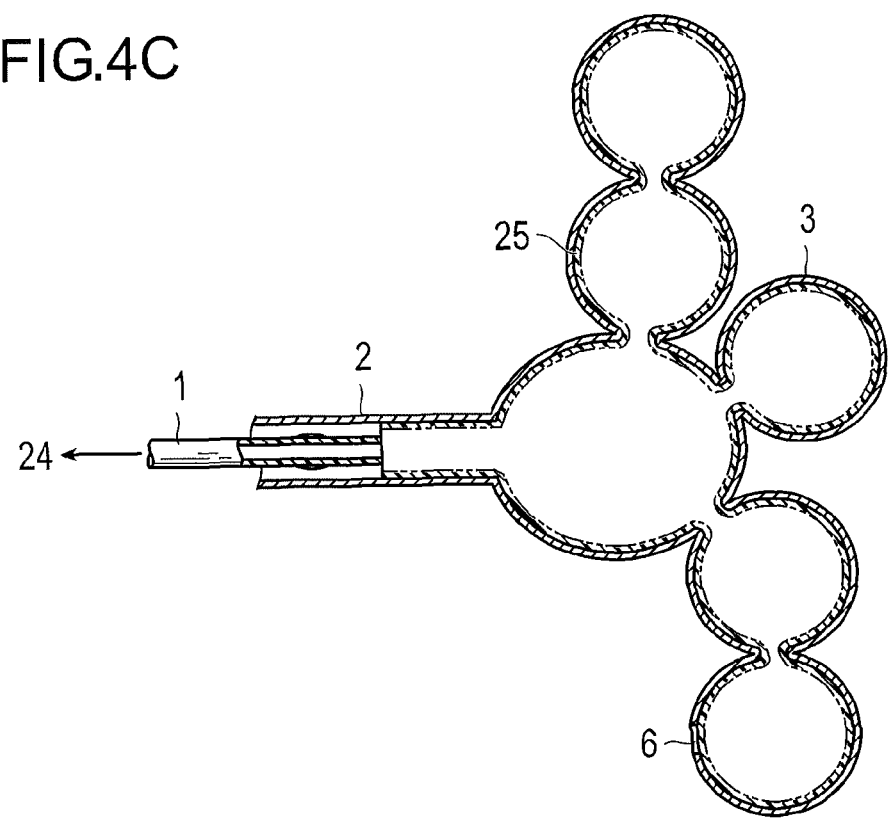

This step, shown in FIGS. 4B to 4E, involves injecting through the catheter 1 the polymeric electrolyte (A) 24 into the respiratory region 2 (FIG. 4B) and then removing by suction an excess of the polymeric electrolyte (A) 24 (FIG. 4C). After removal by suction, the polymeric electrolyte (A) remains in the form of thin film 25 on the inner wall of the alveolar parenchyma 3 suffering from emphysema (FIG. 4C). In addition, the thus formed film 25 of the polymeric electrolyte (A) 24 covers the bypass 6 which might exist in the alveolar parenchyma 3 suffering from emphysema because the bypass is usually a small hole. As the result of the foregoing step, the polymeric electrolyte (A) 24 forms the film 25 that covers the bypass 6. Incidentally, when the polymeric electrolyte (A) 24 is injected or removed by suction, it is desirable to expand the balloon 1a so as to seal the gap between the catheter 1 and the inner wall of the bronchus or bronchiole 2 (FIG. 4B). In this way the polymeric electrolyte (A) 24 can be securely injected into the respiratory region (the alveolar parenchyma suffering from emphysema in the figures) 3 without it flowing backward and it can also be securely removed from the alveolar parenchyma 3 suffering from emphysema without it flowing into the bronchus.

Figure 4D:
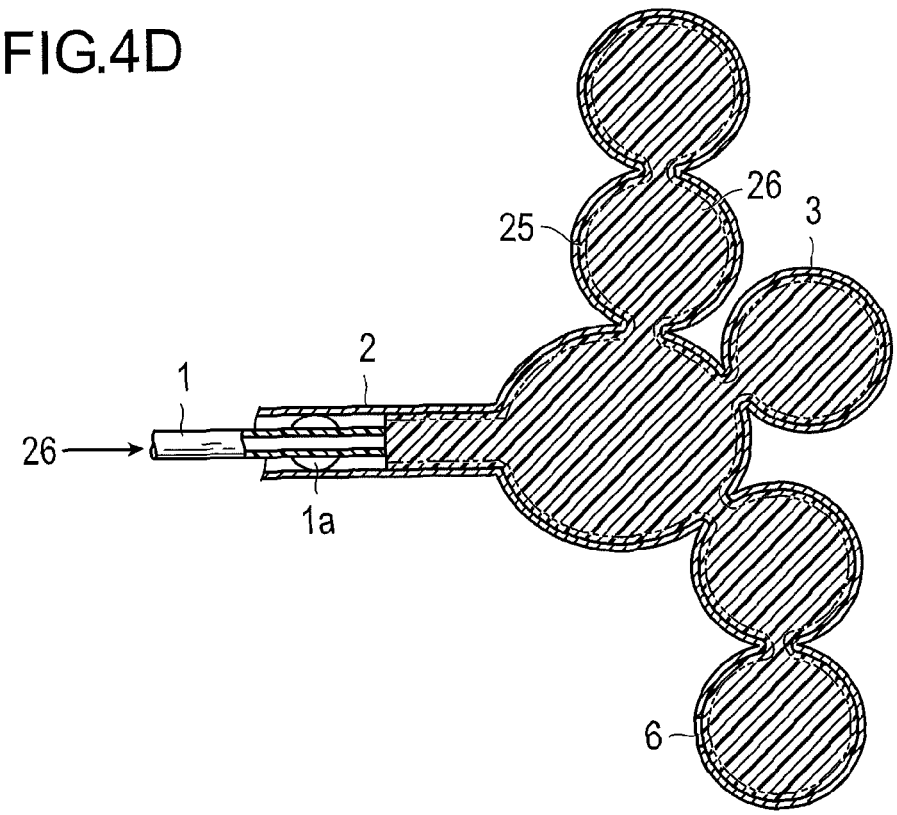
Figure 4E:
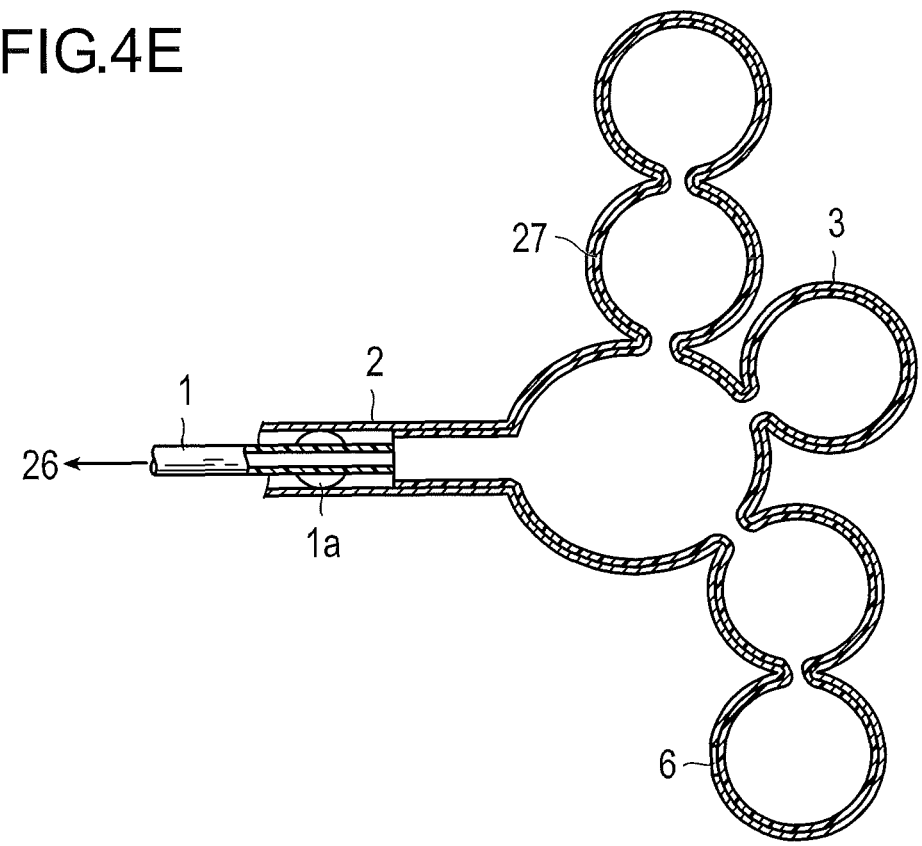

Subsequently, the polymeric electrolyte (B) 26, which has electric charges opposite to those of the polymeric electrolyte (A) 24, is injected into the respiratory region 2 through the catheter 1, so that it comes into contact with the film 25 of the polymeric electrolyte (A) 24 (FIG. 4D). As the result of this procedure, the electric charges (such as positive charges) of the polymeric electrolyte (B) 26 react with the opposite electric charges (such as negative charges) of the polymeric electrolyte (A) 24, thereby forming the ion complex film 27. Therefore, the ion complex film 27 remains on the inner wall of the alveolar parenchyma 3 suffering from emphysema after the polymeric electrolyte (B) 26 has been removed by suction (FIG. 4E). In addition, even in the case where the bypass 6 exists in the alveolar parenchyma 3 suffering from emphysema, the polymeric electrolyte (A) 24 covering the bypass 6 as mentioned above reacts with the polymeric electrolyte (B) 26, thereby forming the ion complex film 27. Consequently, the alveolar parenchyma 3 suffering from emphysema is closed except for the hole communicating with the bronchus (FIG. 4E). Incidentally, when the polymeric electrolyte (B) 26 is injected or removed by suction, it is desirable to expand the balloon 1a so as to seal the gap between the catheter 1 and the inner wall of the bronchus or bronchiole 2 (FIG. 4E). In this way the polymeric electrolyte (B) 26 can be securely injected into the respiratory region (the alveolar parenchyma suffering from emphysema in the figures) 3 without it flowing backward and it can also be securely removed from the alveolar parenchyma 3 suffering from emphysema without it flowing into the bronchus.

The foregoing step may be carried out in such a way that the procedure for injection and removal by suction of the polymeric electrolyte (A) is repeated alternately and the procedure for injection and removal by suction of the polymeric electrolyte (B) is repeated alternately according to need. For example, after the polymeric electrolyte (B) 26 has been removed by suction, the polymeric electrolyte (A) is injected into the respiratory region through the catheter and then an excess of the polymeric electrolyte (A) is removed by suction (not shown). As the result of this procedure, the electric charges (negative charges in the above-mentioned example) of the polymeric electrolyte (B) 26 which were not involved in formation of the ion complex film 27 react with the electric charges (positive charges in the above-mentioned example) of the polymeric electrolyte (A) injected later, so that an additional film is formed. This procedure, therefore, gives a firmer film and permits the alveolar parenchyma suffering from emphysema to shrink securely and readily in the subsequent step. It also securely closes the bypass which might exist. Repetition of that procedure permits easy control of the thickness of the film. Incidentally, the polymeric electrolyte (A) and the polymeric electrolyte (B), which are used in this step, serve as the film-forming agent according to the present invention.

The polymeric electrolyte (A) 24 and the polymeric electrolyte (B) 26 are acceptable so long as they have mutually opposite charges. For example, if the polymeric electrolyte (A) 24 is one which has negative charges, the polymeric electrolyte (B) 26 should be one which has positive charges. If the polymeric electrolyte (A) 24 is one which has positive charges, the polymeric electrolyte (B) 26 should be one which has negative charges The polymeric electrolyte having negative charges is not specifically restricted so long as it has at least one, preferably two or more, anionic groups. It includes, for example, polyamino acid, artificial synthetic polypeptide, polysaccharides such as heparin, hyaluronic acid, chondroitin, pectin, agarose, glycosaminoglycan, cellulose, and starch, and artificial synthetic polysaccharides. The synthetic polymer may have any weight-average molecular weight unrestrictedly, ranging from about 10,000 to 1,000,000, preferably from about 100,000 to 700,000, and more preferably from about 200,000 to 500,000. The polymeric electrolytes mentioned above may be used alone or in combination with one another. Preferable among the examples listed above are heparin, hyaluronic acid, chondroitin, pectin, agarose, and glycosaminoglycan, with heparin, hyaluronic acid being more preferable.

The polymeric electrolyte having negative charges may also be one which is obtained by polymerization of monomers having negative charges. The monomers having negative charges are those which have at least one functional group selected from sulfo group ($-SO_3H$), carboxyl group ($-COOH$), phosphonic acid group ($-PO_3H_2$), and the like, but is not limited thereto.

Unrestricted examples of the monomer having sulfo group ($-SO_3H$) include vinylsulfonic acid (ethylene sulfonic acid), 2-propenesulfonic acid, 3-butenesulfonic acid, 4-pentenesulfonic acid, sulfomethyl (meth)acrylate, 2-sulfoethyl (meth)acrylate, 3-sulfopropyl (meth)acrylate, 2-methyl-3-sulfopropyl (meth)acrylate, 4-sulfobutyl (meth)acrylate, N-(2-sulfoethyl) 4-sulfobutyl (meth)acrylate, 2-(meth)acrylamide-2-methylpropanesulfonic acid, N-(2-sulfoethyl) (meth)acrylamide, N-(1-methyl-2-sulfoethyl) (meth)acrylamide, N-(2-methyl-3-sulfopropyl) (meth)acrylamide, N-(4-sulfobutyl) (meth)acrylamide, 10-sulfodecyl (meth)acrylate, styrenesulfonic acid, (meth) allyl sulfonate, allylsulfonic acid, 3-(meth)acryloxy-2-hydroxypropyl sulfonate, 3-(meth)acryloxy-2-hydroxypropyl sulfophenyl ether, 3-(meth)acryloxy-2-hydroxypropyloxysulfobenzoate, 4-(meth)acryloxybutylsulfonate, (meth)acrylamide methylsulfonic acid, (meth)acrylamide ethylsulfonic acid, and 2-methylpropanesulfonic acid (meth)acrylamide.

Unrestricted examples of the monomer having carboxyl group include (meth) acrylic acid, maleic acid, fumaric acid, glutaconic acid, itaconic acid, crotonic acid, sorbic acid, cinnamic acid, N-(meth)acryloylglycine, N-(meth)acryloylaspartic acid, N-(meth)acryloyl-5-aminosalicylic acid, 2-(meth)acryloyloxyethylhydrogen succinate, 2-(meth)acryloyloxyethylhydrogen phthalate, 2-(meth)acryloyloxyethylhydrogen maleate, 6-(meth)acryloyloxyethylnaphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, and N-(meth)acryloyl-4-aminosalicylic acid.

Unrestricted examples of the monomer having phosphonic acid group include phosphooxyethyl (meth)acrylate, 3-(meth)acryloxypropyl-3-phosphonopropionate, 3-(meth)acryloxypropylphosphonoacetate, 4-(meth)acryloxybutyl-3-phosphonopropionate, 4-(meth)acryloxybutylphosphonoacetate, 5-(meth)acryloxypentyl-3-phosphonopropionate, 5-(meth)acryloxypentylphosphonoacetate, 6-(meth)acryloxyhexyl-3-phosphonopropionate, 6-(meth)acryloxyhexylphosphonoacetate, 10-(meth)acryloxydecyl-3-phosphonopropionate, 10-(meth)acryloxydecylphosphonoacetate, 2-(meth)acryloxyethyl-phenylphosphonate, 2-(meth)acryloyloxyethylphosphonic acid, 10-(meth)acryloyloxydecylphosphonic acid, and N-(meth)acryloyl-ω-aminopropylphosphonic acid.

The monomers mentioned above may be used alone or in combination with one another.

The polymeric electrolyte having positive charges is not specifically restricted so long as it has one or more than one cationic groups. It includes, for example, polyethyleneimine and an organic compound having N,N-dimethylaminoalkyl group in its branched chain. The polymeric electrolyte mentioned above may have any weight-average molecular weight unrestrictedly, ranging preferably from about 10,000 to 1,000,000, and more preferably from about 100,000 to 500,000. The polymeric electrolytes mentioned above may be used alone or in combination with one another. Preferable among the examples listed above are poly(N,N-dimethylaminopropylacrylamide) having a weight-average molecular weight of about 10,000 to 1,000,000, poly(N,N-dimethylaminoethylacrylamide) having a weight-average molecular weight of about 10,000 to 1,000,000, and polyethyleneimine having a weight-average molecular weight of about 10,000 to 1,000,000. More preferable ones are poly(N,N-dimethylaminopropylacrylamide) having a weight-average molecular weight of about 10,000 to 500,000, poly(N,N-dimethylaminoethylacrylamide) having a weight-average molecular weight of about 10,000 to 500,000, and polyethyleneimine having a weight-average molecular weight of about 10,000 to 500,000 (especially about 100,000).

The polymeric electrolyte having positive charges may be obtained by polymerization of monomers having positive charges. The monomers having positive charges are not specifically restricted but they include those which have at least one functional group selected from amino group ($-NH_2$), imino group ($=NH$, $-NH-$), imidazoyl group, and pyridyl group.

The monomers having amino group unrestrictedly include (meth) allylamine, aminoethyl (meth)acrylate, aminopropyl (meth)acrylate, dimethylaminoethyl (meth)acrylate, diethylaminoethyl (meth)acrylate, methylethylaminoethyl (meth)acrylate, dimethylaminopropyl (meth)acrylate, dimethylaminostyrene, diethylaminostyrene, morpholinoethyl (meth)acrylate, and lysine.

The monomers having imino group unrestrictedly include N-methylaminoethyl (meth)acrylate, N-ethylaminoethyl (meth)acrylate, N-t-butylaminoethyl (meth)acrylate, and ethyleneimine.

The monomers having imidazoyl group unrestrictedly include 4-vinylimidazole, N-vinyl-2-ethylimidazole, and N-vinyl-2-methylimidazole.

The monomers having pyridyl group include 2-vinylpyridine, 4-vinylpyridine, and 2-methyl-5-vinylpyridine.

The above-mentioned monomers may be used alone or in combination with one another.

Incidentally, the polymeric electrolyte (A) 24 and the polymeric electrolyte (B) 26 may be constructed of not only the above-mentioned monomers having negative charges or positive charges but also any other known monomers as exemplified below which is not specifically restricted. Particularly, monomers having carboxyl groups in the form of salt such as sodium salt, potassium salt, and ammonium salt; Monomers having sulfo groups in the form of monovalent metal salt, divalent metal salt, ammonium salt, and organic amine salt; (poly)alkyleneglycol di(meth)acrylates, such as triethylene glycol di(meth)acrylate, (poly)ethylene glycol di(meth)acrylate, polypropylene glycol di(meth)acrylate, and (poly)ethyleneglycol (poly)propylene glycol di(meth)acrylate; difunctional (meth)acrylates, such as hexanediol di(meth)acrylate, trimethylolpropane tri(meth)acrylate, and trimethylolpropane di(meth)acrylate; (poly)alkyleneglycol dimaleates, such as triethyleneglycol dimaleate and polyethyleneglycol dimaleate; esters of unsaturated monocarboxylic acids and alcohols having 1 to 4 carbon atoms, such as methyl (meth) acrylate, ethyl (meth)acrylate, propyl (meth)acrylate, glycidyl (meth)acrylate, methyl crotonate, ethyl crotonate, and propyl crotonate; amides of unsaturated monocarboxylic acids and amines having 1 to 30 carbon atoms, such as methyl (meth)acrylamide; vinyl aromatics, such as styrene, $\alpha$-methylstyrene, vinyltoluene, and p-methylstyrene; alkanediol mono(meth)acrylates, such as 1,4-butanediol mono(meth)acrylate, 1,5-pentanediol mono(meth)acrylate, and 1,6-hexanediol mono(meth)acrylate; dienes, such as butadiene, isoprene, 2-methyl-1,3-butadiene, and 2-chloro-1,3-butadiene; unsaturated amides, such as (meth) acrylamide, (meth) acrylalkylamide, N-methylol (meth) acrylamide, and N,N-dimethyl (meth)acrylamide; unsaturated nitriles, such as (meth) acrylonitrile and $\alpha$-chloroacrylonitrile; unsaturated esters, such as vinyl acetate and vinyl propionate; and unsaturated amines, such as aminoethyl (meth)acrylate, methylaminoethyl (meth)acrylate, dimethylaminoethyl (meth)acrylate, dimethylaminopropyl (meth)acrylate, dibutylaminoethyl (meth) acrylate, and vinylpyridine. These monomers may be used alone or in combination with one another. In the case where the polymeric electrolyte has constituents derived from additional monomers, the amount of the additional monomers is not specifically restricted so long as it is small enough not to adversely affect the monomers having positive charges or negative charges. It should preferably be 1 to 10 wt % in the total amount.

According to the present invention, the polymeric electrolyte (A) and the polymeric electrolyte (B) have mutually opposite charges; therefore, the above-mentioned monomers should be properly selected for production of the polymeric electrolyte (A) and polymeric electrolyte (B) so that the polymeric electrolyte (A) and polymeric electrolyte (B) are charged oppositely.

The polymeric electrolytes according to the present invention may be produced by any known unrestricted method for polymerization. It is usually produced from the above-mentioned monomers by polymerization with the help of a polymerization initiator. Polymerization procedure of the monomers may be accomplished which is not specifically restricted in any way, such as solution polymerization and bulk polymerization. If the polymeric electrolytes according to the present invention are block copolymers or graft copolymers, they can be produced unrestrictedly by any of living polymerization, polymerization from macro monomers, polymerization with the help of a polymeric polymerization initiator, and polycondensation.

The polymeric electrolyte (A) or the polymeric electrolyte (B) may be injected as such into the respirator region or may be used in the form of solution or dispersion in a proper solvent. The solvent for solution or dispersion is not specifically restricted so long as it is capable of dissolving or dispersing the polymeric electrolyte (A) or the polymeric electrolyte (B) and safe. Examples of the solvent include water, dimethylsulfoxide, dimethylformamide, glycols such as ethylene glycol, diethylene glycol, propylene glycol, triethylene glycol, polyethylene glycol, and polypropylene glycol, and fats and oils such as olive oil, castor oil, squalane, and lanolin. The above-mentioned solvents may be used alone or in combination with one another. Preferable among the above-mentioned solvents are water, dimethylsulfoxide and dimethylformamide, which are safe, and water is more desirable.

No specific restrictions are imposed on the concentrations of the polymeric electrolyte (A) and the polymeric electrolyte (B) in the solution or dispersion to be injected into the respiratory region. A preferred concentration is 5 to 50 wt %. This concentration is desirable for the solution or dispersion to readily and efficiently form the film on the inner wall of the alveolar parenchyma suffering from emphysema. The polymeric electrolyte (A) and the polymeric electrolyte (B) may have identical or different concentrations in their solution or dispersion.

The polymeric electrolyte (A) and the polymeric electrolyte (B) may be mixed together in any ratio unrestrictedly. The mixing ratio should preferably be from 1:0.1 to 1:5, more preferably from 1:0.5 to 1:2 (by mass). This mixing ratio is desirable for the polymeric electrolyte (A) and the polymeric electrolyte (B) to react with each other efficiently, thereby forming the ion complex film over the entire surface of the inner wall of the alveolar parenchyma suffering from emphysema.

The polymeric electrolyte (A) or the polymeric electrolyte (B) may be introduced into the alveolar parenchyma suffering from emphysema in any amount unrestrictedly so long as the polymeric electrolyte (A) and the polymeric electrolyte (B) sufficiently fill the alveolar parenchyma suffering from emphysema. For example, injection of the polymeric electrolyte (A) or the polymeric electrolyte (B) should be suspended as soon as an increase in injection pressure of the polymeric electrolyte (A) or the polymeric electrolyte (B) is detected. Likewise, the polymeric electrolyte (A) and the polymeric electrolyte (B) may be removed by suction from the alveolar parenchyma suffering from emphysema in any amount unrestrictedly so long as they can be substantially removed from the alveolar parenchyma suffering from emphysema. For example, after injection of the polymeric electrolyte (A) or the polymeric electrolyte (B), removal of the excess polymeric electrolyte (A) or the polymeric electrolyte (B) should be suspended as soon as it becomes impossible to continue suction. Incidentally, the polymeric electrolyte (A) or the polymeric electrolyte (B) may be injected and removed through either the same lumen or the different lumens of the catheter, but using the same lumen is desirable for easy operation. The polymeric electrolyte (A) 24 and the polymeric electrolyte (B) 26 may be injected and removed once or preferably several times respectively, so that they entirely cover the inner wall of the alveolar parenchyma suffering from emphysema.

Injection of the polymeric electrolyte (A) 24 and the polymeric electrolyte (B) 26 into the alveolar parenchyma suffering from emphysema may be followed by injection of an adequate gas, so that the previously injected polymeric electrolytes uniformly cover the surface of the alveolar parenchyma 3 suffering from emphysema. A desirable gas for this purpose is one which is less viscous than the polymeric electrolytes, so that it permits the polymeric electrolyte to form a uniform film on the surface of the alveolar parenchyma. The gas may be selected unrestrictedly from air, oxygen, carbon dioxide, carbon monoxide, nitrogen, helium, and argon.

The polymeric electrolyte (A) 24 and the polymeric electrolyte (B) 26 may remain in contact with each other in the film 25 for any unrestricted period of time. Duration of 1 to 10 minutes is desirable for the polymeric electrolyte (A) 24 and the polymeric electrolyte (B) 26 to react completely with each other.

After reaction is completed between the polymeric electrolyte (A) 24 and the polymeric electrolyte (B) 26, the polymeric electrolyte (B) 26 is removed by suction. Since the alveolar parenchyma suffering from emphysema is closed except for the hole communicating with the bronchus or bronchiole, the polymeric electrolyte (B) 26 is removed somewhat together with the lumen of the alveolar parenchyma 3 suffering from emphysema. Thus the alveolar parenchyma 3 shrinks as the result of removal by suction.

The film-forming agents used in the above-mentioned steps (b-1) to (b-3) are slow in curing to form the film. Such steps (b-1) to (b-3) are particularly desirable because the alveolar parenchyma suffering from emphysema is kept shrunk until curing after the subsequent step (c).

3. Step (c)

This step is intended to shrink the alveolar parenchyma (pulmonary alveoli or alveolar sacs) suffering from emphysema which had the film formed on the inner wall thereof by the previous step (b). As the result of this step, the alveolar parenchyma suffering from emphysema rapidly shrinks, so that air remaining in the alveolar parenchyma suffering from emphysema is efficiently removed. The film-forming agents used in the above-mentioned steps (b-1) to (b-3) are slow to cure to form the film and hence they complete film formation after shrinkage therefore they keep the alveolar parenchyma suffering from emphysema shrunk and efficiently reduce the volume of the alveolar parenchyma and permit the patient to maintain this reduced volume at the time of respiration. This alleviates and prevents the overexpansion of the lung due to emphysema or occlusion of air-supply bronchi which weakens the patient. The result is that the alveolar parenchyma suffering from emphysema can be made smaller than its original size, and this alleviates and prevents the pressure and occlusion of the bronchi by the peripheral alveolar parenchyma. In addition, the above-mentioned steps (a) to (c) according to the present invention enable treatment through a catheter without the need for surgical treatment, and this leads to a reduced burden on the patient.

This step is designed to shrink the alveolar parenchyma (alveoli or alveolar sacs) suffering from emphysema in any unrestricted way. For example, one of the following steps (c-1) to (c-4) is desirable.

(c-1): This step involves filling through the catheter a reactive gas into the alveoli or alveolar sacs, closing the bronchus or bronchiole with an adequate closing means, and injecting an agent that absorbs said reactive gas into the alveoli or alveolar sacs.

(c-2): This step, which employs a film-forming agent which forms a foam-like film, is designed to eliminate foams resulting from the film-forming agent or remove by suction the foam-like film-forming agent through the catheter, after the step (b) mentioned above.

(c-3): This step involves removing by suction through the catheter the gas remaining in the alveoli or alveolar sacs, and (c-4): This step involves removing by suction the film-forming agent from the alveoli or alveolar sacs.

Incidentally, the step (c-4) also involves removing by suction the film-forming agent like the foregoing steps (b-1) to (b-3); therefore, the step (c-4) may be omitted if removing by suction is carried out in the steps (b-1) to (b-3).

The following is a description of the preferred methods for carrying out the steps (c-1) to (c-3); however, they are not intended to restrict the scope of the present invention.

3-1. Step (c-1)

Figure 2D:
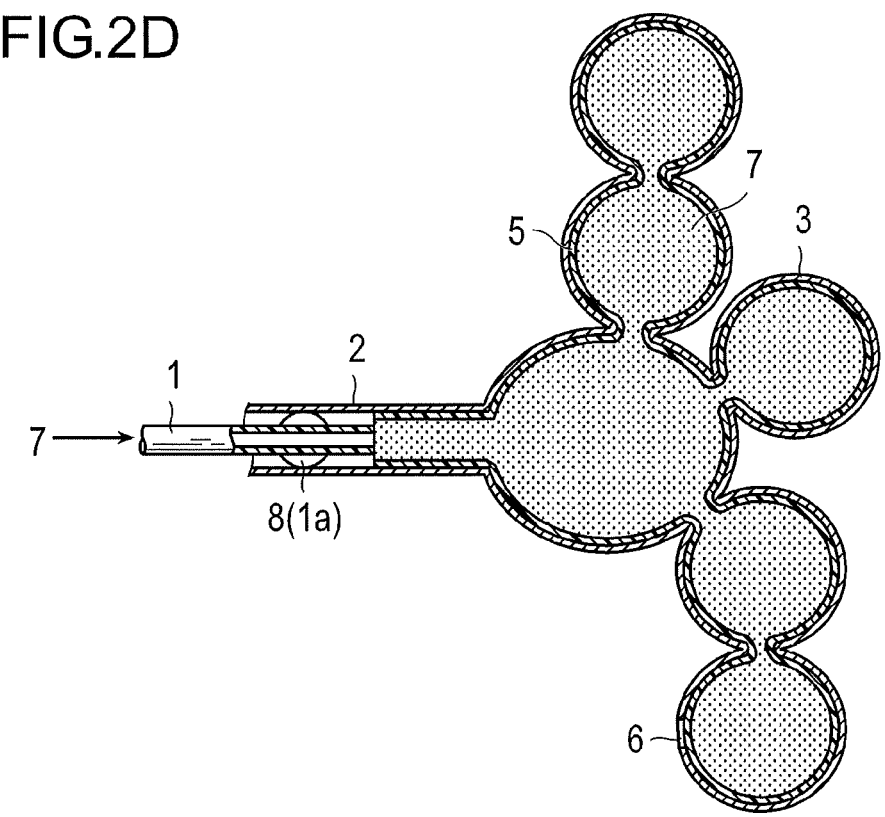
Figure 2E:
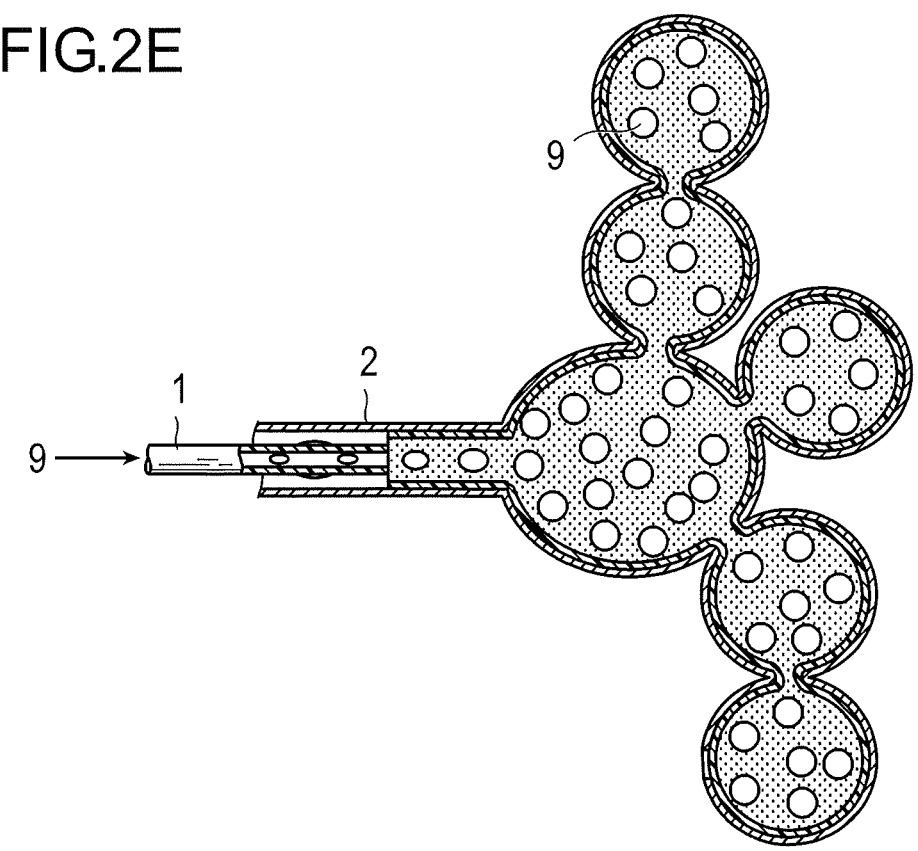
Figure 2F:
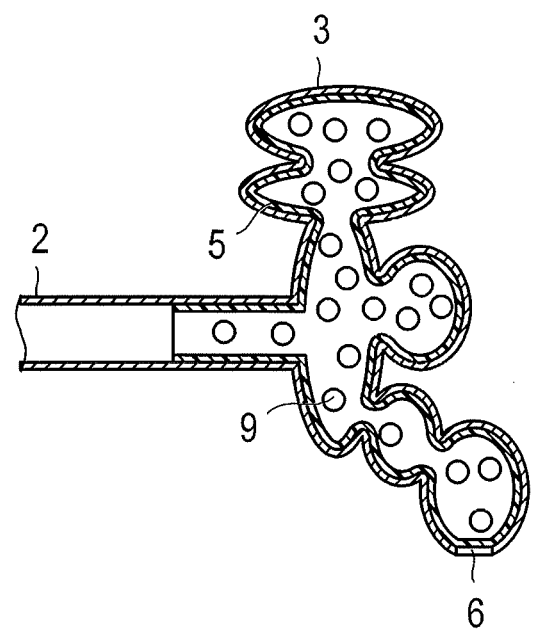

This step, as shown in FIGS. 2D to 2F, involves injecting the reactive gas 7 into the respiratory region 2 through the catheter 1, thereby filling the reactive gas 7 into the pulmonary alveoli or alveolar sacs (the alveolar parenchyma suffering from emphysema) 3. At the time of filling of the reactive gas 7, it is desirable to seal, by expanding the balloon 1a, the gap between the catheter 1 and the inner wall of the bronchus or bronchiole 2 (FIG. 2D). This ensures the filling of the reactive gas 7. Then, the bronchus or bronchiole 2 is closed by using the means 8 for closing the bronchus or bronchiole (FIG. 2D). Closing the bronchus or bronchiole 2 in this way allows the reactive gas 7 to enter sufficiently into the alveolar parenchyma 3 suffering from emphysema, so that the reactive gas 7 reacts efficiently with the film-forming agent 3 in the film 5. Further, the gas absorbing agent 9 that absorbs the reactive gas is injected into the pulmonary alveoli or alveolar sacs (the alveolar parenchyma suffering from emphysema) 3 (FIG. 2E). Absorption of the reactive gas by the gas absorbing agent 9 causes the alveolar parenchyma suffering from emphysema to aggregate, and the alveolar parenchyma suffering from emphysema decreases in volume (FIG. 2F). An efficient and rapid decrease in the volume of the alveolar parenchyma can be achieved because the film 5 that suppresses and prevents air leakage has been formed in the alveolar parenchyma suffering from emphysema by the foregoing step (b). Incidentally, the gas absorbing agent 9 may be removed by suction. However, the gas absorbing agent is not always necessarily removed as shown in FIG. 2F because the shrunk alveolar parenchyma does not function as the pulmonary alveoli or alveolar sac.

The reactive gas 7 is not specifically restricted but should preferably be one which is reactive with the film-forming agent 3 in the film formed by the step (b). In this case, the reactive gas 7 reacts with the film-forming agent 3 in the film formed by the step (b), thereby allowing curing to proceed slowly and terminate after the alveolar parenchyma suffering from emphysema has shrunk. This permits the alveolar parenchyma suffering from emphysema to maintain its reduced lung volume. The reactive gas used for this purpose includes oxygen and carbon dioxide. The above-mentioned reactive gas may be used in the form of a single gas or a mixture of gases. A preferable reactive gas is oxygen, which naturally exists in the lung and is safe even though it is taken into the body.

The reactive gas may be introduced into the alveolar parenchyma suffering from emphysema in any amount which is sufficient to fill it, and not specifically restricted. For example, injection of the reactive gas should be suspended when an increase in the injection pressure of the reactive gas is detected. Introduction of the reactive gas into the alveolar parenchyma suffering from emphysema may be accomplished by using the lumen of the catheter which is identical with or different from the one used for introduction of the film-forming agent.

The reactive gas introduced into the alveolar parenchyma suffering from emphysema may rem there for any length of time, preferably 1 to 10 minutes, which is enough for the reactive gas to completely react with the film-forming agent in the film.

The means to close the bronchus or bronchiole (closing means) 8 is not specifically restricted so long as it is capable of closing temporarily or permanently. The temporal closing means is not specifically restricted and temporary closing may be accomplished by means of the balloon 1a attached to the catheter 1, as shown in FIG. 2D. If the balloon 1a is expanded when the reactive gas 7 is filled, the bronchus or bronchiole 2 should be kept closed after the reactive gas 7 has been filled. The permanent closing means is also not specifically restricted and permanent closing may be accomplished by using a soft material like sponge for closing the bronchus or bronchiole 2. Closing in this manner alleviates and prevents the reactive gas 7 from leaking from the alveolar parenchyma 3 suffering from emphysema, thereby permitting efficient reaction between the reactive gas 7 and the film-forming agent 3. The closing means 8 may be placed at any position, which is close to the end of the catheter or at the bronchus (proximal side). If the end of the catheter is in the bronchus, the catheter should be positioned such that the closing means does not go beyond the branch of the bronchus on the proximal side. This prevents the reactive gas from flowing into the bronchus on the proximal side. Incidentally, it is permissible to previously close the bronchus or bronchiole 2 before introduction of the reactive gas. This alleviates and prevents the reactive gas from flowing backward into the trachea (proximal side) of the bronchus or bronchiole 2, thereby permitting efficient introduction of the reactive gas into the aimed alveolar parenchyma suffering from emphysema. The means to close the bronchus or bronchiole is not specifically restricted, for example, the same one as the closing means 8 mentioned above may be used.

The gas-absorbing agent 9 is not specifically restricted so long as it is capable of absorbing the reactive gas 7. It is selected from the following examples according to the kind of the reactive gas 7. Silica, ceramics, porous ceramics, magnesia, titania, calcium silicate, activated carbon; iron powders such as pure iron powder, cast iron powder, steel powder, reduced iron powder, sprayed iron powder, spongy iron powder, electrolytic iron powder, and iron alloy powder, aluminum powder, magnesium powder, silicon fine powder; L-ascorbic acid, isoascorbic acid (erythorbic acid), alkali metal salt thereof, and alkaline earth metal salt thereof; polyhydric alcohols such as glycerin, ethylene glycol, and propylene glycol; phenol compounds such as catechol, resorcin, hydroquinone, gallic acid, pyrogallol, and tocopherol; and reducing sugars such as glucose, fructose, sorbitol, and xylose. They may be used alone or in combination with one another. Preferable among the foregoing examples are iron powder, ceramics, and porous ceramics, which are safe to use.

Iron powder as one of the above-mentioned gas-absorbing agents should preferably be used in combination with a pro-oxidant for better oxygen absorption. The pro-oxidant may be selected unrestrictedly from halides of alkali metal or alkaline earth metal such as NaCl, $CaCl_2$, and $MgCl_2$, halides of ion-exchange resin, hydrochloric acid, and hypochlorite. The pro-oxidant should preferably be used in an amount of 0.01 to 20 parts by weight for 100 parts by weight of iron powder.

The gas-absorbing agent should be introduced into the alveolar parenchyma affected with emphysema in any unrestricted amount enough to reduce the volume of the alveolar parenchyma affected with emphysema which has sufficiently absorbed the reactive gas. An adequate amount is determined according to the volume of the alveolar parenchyma affected with emphysema. Alternatively, injection of the gas-absorbing agent may be suspended as soon as an increase in injection pressure of the gas-absorbing agent is detected. Introduction of the gas-absorbing agent into the alveolar parenchyma affected with emphysema may be carried out through the lumen of the catheter which is identical with the one used for introduction of the film-forming agent or reactive gas or different from the one used for introduction of the film-forming agent or reactive gas.

The gas-absorbing agent which has been introduced into the alveolar parenchyma affected with emphysema should remain there for an unrestricted length of time, preferably ranging from 1 to 10 minutes, which is enough for the gas-absorbing agent to sufficiently absorb the reactive gas to reduce the volume of the alveolar parenchyma affected with emphysema.

3-2. Step (c-2)

Figure 3E:
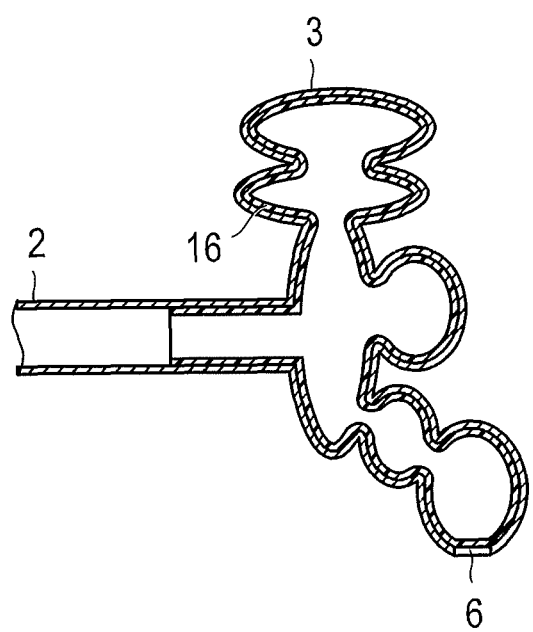

This step employs a film-forming agent which forms a foam-like film. Following the step (b) mentioned above, the foam-like film-forming agent 14 remaining uncured has its foaming gas released from the body or absorbed into the body, so that the alveolar parenchyma 3 affected with emphysema decreases in volume as foams disappear. In this case, the step shown in FIG. 3D is skipped from the step of FIG. 3C to the step of FIG. 3E (FIG. 3C→FIG. 3E). The foam-like film-forming agent is produced from the film-forming agent used in the step (b) mentioned above, particularly the material 14 used in the step (b-2) mentioned above which cures upon reaction with water or divalent metal ions, by incorporation with any gas of nitrogen, helium, argon, carbon monoxide, carbon dioxide, and oxygen, as a foaming agent, and foaming. The foam-like film-forming agent may also be produced by incorporating the film-forming agent with sodium hydrogen carbonate and citric acid in powder form dispersed therein. The foregoing is a mere example of the method for production of the foam-like film-forming agent.

Foams that occur while the foam-like film-forming agent 14 has not yet cured may be allowed to disappear naturally or forced to disappear with the help of a defoaming agent. Foams that occur after the foam-like film-forming agent has cured should preferably be allowed to disappear naturally by dif fusion. The defoaming agent used for the latter purpose may be selected unrestrictedly from defoaming agents used in the medical field such as lower alcohols such as methanol, ethanol, isopropanol, and butanol; silicone compounds such as silicone oil; and organic polar compounds such as 2-ethylhexanol, diisobutylcarbinol, amyl alcohol, tributyl phosphate, octylphosphate sodium, metal salt of stearic acid, metal salt of palmitic acid, isoamyl stearate, diglycol laurate, sorbitan trioleate, polyoxyethylene sorbitanmonolaurate, Pluronic nonionic surfactant, polyalkylene glycol and derivatives thereof. These defoaming agents may be used alone or in combination with one another. Preferable among these defoaming agents are derivatives of polyalkylene glycol, which excel in defoaming performance. The defoaming agent should be introduced into the alveolar parenchyma affected with emphysema in an amount sufficient to defoam the uncured foam-like film-forming agent to such an extent as required to sufficiently reduce the volume of the alveolar parenchyma affected with emphysema. The amount of the defoaming agent should preferably be about 0.001 to 5 wt % of the amount of the initially introduced foam-like film-forming agent. Introduction of the defoaming agent into the alveolar parenchyma affected with emphysema may be carried out through the lumen of the catheter which is identical with the one used for introduction of the film-forming agent or different from the one used for introduction of the film-forming agent.

The foam-like film-forming agent 14 remaining uncured may be removed by suction through the catheter 1, so that the volume of the alveolar parenchyma 3 affected with emphysema is reduced. In this case, the step of FIG. 3C continues to the step of FIG. 3E through the step of FIG. 3D (FIG. 3C→FIG. 3D→FIG. 3E). The foam-like film-forming agent 14 remaining uncured should be removed in any amount substantially available for the alveolar parenchyma affected with emphysema. It may be sucked out until suction of the foam-like film-forming agent becomes impossible to continue. Introduction and removal of the foam-like film-forming agent may be carried out through the lumen of the catheter which is identical with the one used for introduction of the film-forming agent or different from the one used for introduction of the film-forming agent.

3-3. Step (c-3)

Figure 4F:
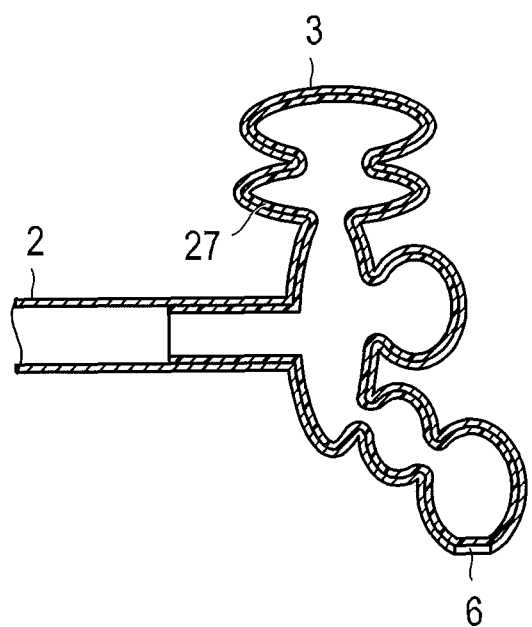

This step is intended to remove by suction through the catheter any gas remaining in the pulmonary alveoli or alveolar sacs (FIG. 4F). There may exist an instance in which the alveolar parenchyma 3 affected with emphysema remains expanded even after the film-forming agent has been removed by suction. In this case, residual gas in the alveolar parenchyma 3 affected with emphysema should be removed by suction through the catheter, so that the volume of the alveolar parenchyma affected with emphysema is reduced efficiently and rapidly because the alveolar parenchyma 3 affected with emphysema is closed except for holes communicating with the bronchus or bronchiole 2. Removal by suction of residual gas from the alveolar parenchyma 3 affected with emphysema should be continued until suction becomes impossible to continue.

3-4. Step (c-4)

This step is intended to remove by suction the film-forming agent from the pulmonary alveoli or alveolar sacs. Since the alveolar parenchyma affected with emphysema is closed except for holes communicating with the bronchus or bronchiole as mentioned above, the alveolar parenchyma 3 shrinks according as the film-forming agent is removed by suction. This step is very simple and hence desirable. If the alveolar parenchyma 3 does not shrink sufficiently even after this step, it is desirable to perform at least one of the above-mentioned steps (c-1) to (c-3).

The foregoing is a detailed description of the step (a), the steps (b-1) to (b-3), and the steps (c-1) to (c-3). These steps may be employed in any combination. Examples of the desirable combination are as follows.

Steps (a) and (b-1); steps (a) and (b-2); steps (a) and (b-3); steps (a), (b-1), and (c-1); steps (a), (b-1), and (c-3); steps (a), (b-2), and (c-2); and steps (a), (b-3), and (c-3). Examples of the more desirable combination are as follows. Steps (a) and (b-1); steps (a) and (b-2); steps (a) and (b-3); steps (a), (b-1), and (c-1); steps (a), (b-2), and (c-2); and steps (a), (b-3), and (c-3).

As mentioned above, the method for treatment according to the present invention is designed to efficiently remove air remaining in the alveolar parenchyma affected with emphysema, thereby maintaining the volume reduced by respiration. Therefore, it enables one to alleviate and prevent over-expansion of the lung which weakens the patient by emphysema or occlusion of air-supply bronchi. In addition, it permits the alveolar parenchyma affected with emphysema to become smaller than its original size, with the neighboring bronchi being alleviated and prevented from pressure or occlusion by their surrounding alveolar parenchyma. Moreover, the method for treatment according to the present invention relieves the patient from burden because it relies on operation through the catheter without surgical operation. The present invention produces additional effects of forming the film on the inner wall of the alveolar parenchyma affected with emphysema, thereby restoring the elasticity of the alveolar parenchyma affected with emphysema and alleviating and preventing the over-expansion of the lung.

EXAMPLES

The present invention will be described below in more detail with reference to the following examples which demonstrate the method for transbronchially coating the tissue of the alveolar sac (air sac) or pulmonary alveoli, the tissue of the terminal bronchiole, and the tissue of the bypass which exist at arbitrary positions. The examples are not intended to restrict the scope of the present invention.

Example 1

The first step started with insertion of a balloon catheter 1 into the lumen of the bronchiole 2 as shown in FIG. 2A through the working lumen of the bronchoscope (not shown). This balloon catheter is PTCA balloon catheter of OTW type (Ryujin Plus OTW (registered trademark), Medical Instrument Approval Number 21600BZZ00035, made by TERUMO CORPORATION) which is designed for treatment of angiostenosis of the vascular lumen in the cardiovascular region. The working lumen of the bronchoscope has a guide wire with an outside diameter of 0.014 inches (Runthrough (registered trademark), made by TERUMO CORPORATION) which was previously inserted therein. The tip of this guide wire was advanced to the vicinity of the intended alveolar parenchyma 3 affected with emphysema with the help of X ray fluoroscopy. Then, the catheter was advanced along the guide wire to the vicinity of the intended alveolar parenchyma 3 affected with emphysema with the help of X ray fluoroscopy. Finally, the guide wire was pulled out.

As shown in FIG. 2B, an aqueous solution (2 wt %) of gelatin was filled into a syringe as the film-forming agent 4. The balloon 1a was expanded with air by means of a syringe connected to the lumen for balloon expansion arranged at the base end of the catheter 1, so that the bronchiole 2 was closed. The aqueous solution of gelatin was injected into the lumen of the alveolar parenchyma 3 affected with emphysema through the lumen of the catheter 1. Injection of the aqueous solution of gelatin was suspended when the injection pressure of the syringe increased. In this way, a sufficient amount of the gelatin aqueous solution was injected into the lumen of the alveolar parenchyma 3. The thus injected aqueous solution of gelatin was allowed to stand for five minutes, so that the gelatin cured. The gelatin aqueous solution 4 was removed by suction. That portion of the gelatin aqueous solution 4 which remained uncured was removed by suction efficiently because the bypass 6 was closed by the film 5 of gelatin which was formed on the inner wall of the alveolar parenchyma 3 affected with emphysema (FIG. 2C).

The balloon 1a of the catheter 1 was expanded with air in the same way as mentioned above, so that the bronchiole 2 was closed, and then oxygen as the reactive gas 7 was injected through the inflation lumen, as shown in FIG. 2D. The reactive gas 7 was filled efficiently into the alveolar parenchyma 3 because the lumen of the alveolar parenchyma 3 was coated with the film-forming agent 4.

Iron powder as the gas-absorbing agent 9 was sprayed into the lumen of the alveolar parenchyma 3 affected with emphysema through the lumen which capable of gas delivery of the catheter 1, as shown in FIG. 2E. The amount of the sprayed iron powder was about 3.2 mg per 1 mL of the volume of the lumen of the alveolar parenchyma 3. The sprayed iron powder absorbed the gas remaining in the alveolar parenchyma 3 affected with emphysema, thereby shrinking the alveolar parenchyma 3 affected with emphysema and reducing the volume thereof (FIG. 2F). It was also confirmed that the alveolar parenchyma 3 affected with emphysema kept its reduced volume because the gelatin continued to cure with the reduced volume maintained (FIG. 2F).

Example 2

The first step started with insertion of a balloon catheter 1 into the lumen of the bronchiole 2 (as shown in FIG. 3A) through the working lumen of the bronchoscope (not shown). This balloon catheter 1 is PTCA balloon catheter of OTW type (Ryuj in Plus OTW (registered trademark), Medical Instrument Approval Number 21600BZZ00035, made by TERUMO CORPORATION) which is designed for treatment of angiostenosis of the vascular lumen in the cardiovascular region. The working lumen of the bronchoscope has a guide wire with an outside diameter of 0.014 inches (Runthrough (registered trademark), made by TERUMO CORPORATION) which was previously inserted therein. The tip of this guide wire was advanced to the vicinity of the intended alveolar parenchyma 3 affected with emphysema with the help of X ray fluoroscopy. Then, the catheter was advanced along the guide wire to the vicinity of the intended alveolar parenchyma 3 affected with emphysema with the help of X ray fluoroscopy. Finally, the guide wire was pulled out.

As shown in FIG. 3B, octyl-α-cyanoacrylate prepared from sodium hydrogen carbonate and citric acid, both dispersed therein in powder form was filled into a syringe as the foam-like film-forming agent 14. At the time, low-molecular-weight polyethylene glycol was added thereinto to reduce viscosity of the solution of octyl-α-cyanoacrylate. The balloon 1a was expanded with air by means of the indeflator connected to the lumen for balloon expansion arranged at the base end of the catheter 1, so that the bronchiole 2 was closed. The octyl-α-cyanoacrylate was injected into the lumen of the alveolar parenchyma 3 affected with emphysema through the lumen of the catheter 1 from the syringe. Injection of the octyl-α-cyanoacrylate was suspended when the injection pressure of the syringe increased. In this way, a sufficient amount of octyl-α-cyanoacrylate was injected into the lumen of the alveolar parenchyma 3. The thus injected octyl-α-cyanoacrylate rapidly cured upon reaction with water 15 present on the surface of the alveolar parenchyma 3 affected with emphysema, thereby forming the film 16 on the inner wall of the alveolar parenchyma 3 (FIG. 3C). At the same time, it gave rise to foams of carbon dioxide gas.

The reaction of octyl-α-cyanoacrylate with water 15 present on the surface of the alveolar parenchyma 3 affected with emphysema was observed by adding water dropwise to octyl-α-cyanoacrylate placed on a slide glass simultaneously with the start of injection of the octyl-α-cyanoacrylate. After complete film formation was confirmed, the octyl-α-cyanoacrylate was removed by suction (FIG. 3D). It was possible to efficiently remove by suction the octyl-α-cyanoacrylate 14 remaining unreacted because the bypass 6 was closed by the film formation.

It was confirmed that the volume of the alveolar parenchyma 3 affected with emphysema decreased as the octyl-α-cyanoacrylate was removed by suction and the carbon dioxide foams that occurred in the octyl-α-cyanoacrylate disappeared. It was also confirmed that the alveolar parenchyma 3 affected with emphysema kept its reduced volume because the octyl-α-cyanoacrylate continued to cure with the reduced volume maintained (FIG. 3E).

Example 3

As shown in FIG. 3A, the first step started with insertion of a balloon catheter 1 into the lumen of the bronchiole 2 through the working lumen of the bronchoscope (not shown). This balloon catheter 1 is PTCA balloon catheter of OTW type (Ryuj in Plus OTW (registered trademark), Medical Instrument Approval Number 21600BZZ00035, made by TERUMO CORPORATION) which is designed for treatment of angiostenosis of the vascular lumen in the cardiovascular region. The working lumen of the bronchoscope has a guide wire with an outside diameter of 0.014 inches (Runthrough (registered trademark), made by TERUMO CORPORATION) which was previously inserted therein. The tip of this guide wire was advanced to the vicinity of the intended alveolar parenchyma 3 affected with emphysema with the help of X ray fluoroscopy. Then, the catheter was advanced along the guide wire to the vicinity of the intended alveolar parenchyma 3 affected with emphysema with the help of X ray fluoroscopy. Finally, the guide wire was pulled out.

As shown in FIG. 3B, an aqueous solution (10 wt %) of alginic acid incorporated with carbon dioxide was filled into a syringe as the foam-like film-forming agent 14. Carbon dioxide foams were made by dissolving sodium hydrogen carbonate into the aqueous solution of alginic acid and then adding dilute hydrochloric acid thereinto. The balloon 1a was expanded with air by means of the indeflator connected to the lumen for balloon expansion arranged at the base end of the catheter 1, so that the bronchiole 2 was closed. The aqueous solution of alginic acid was injected into the lumen of the alveolar parenchyma 3 affected with emphysema through the lumen of the catheter 1 from the syringe. Injection of the aqueous solution of alginic acid was suspended when the injection pressure of the syringe increased. In this way, the aqueous solution of alginic acid was sufficiently injected into the lumen of the alveolar parenchyma 3. The thus injected alginic acid rapidly cured upon reaction with calcium ions 15 present on the surface of the alveolar parenchyma 3 affected with emphysema, thereby forming the film 16 on the inner wall of the alveolar parenchyma 3 (FIG. 3C).

Injection of the aqueous solution of alginic acid was followed by standing for three minutes during which the film formed. After that, the aqueous solution of alginic acid was removed by suction (FIG. 3D). It was possible to efficiently remove by suction the aqueous solution of alginic acid 14 remaining unreacted because the bypass 6 was closed by the film formation.

It was confirmed that the volume of the alveolar parenchyma 3 affected with emphysema decreased as the aqueous solution of alginic acid was removed by suction and the carbon dioxide foams that occurred in the aqueous solution of alginic acid disappeared. As an excess of the aqueous solution of alginic acid is removed by suction, the concentration of calcium ions increased on the surface 15 of the alveolar parenchyma 3 affected with emphysema. The result was that reaction between alginic acid 14 and calcium ions 15 proceeded effectively on the surface of the alveolar parenchyma 3 affected with emphysema to form the film, and the alveolar parenchyma 3 affected with emphysema maintained its reduced volume (FIG. 3E).

Example 4

The first step started with insertion of a balloon catheter 1 into the lumen of the bronchiole 2 (as shown in FIG. 4A) through the working lumen of the bronchoscope (not shown). This balloon catheter 1 is PTCA balloon catheter of OTW type (Ryuj in Plus OTW (registered trademark), Medical Instrument Approval Number: 21600BZZ00035, made by TERUMO CORPORATION) which is designed for treatment of angiostenosis of the vascular lumen in the cardiovascular region. The working lumen of the bronchoscope has a guide wire (Runthrough (registered trademark), made by TERUMO CORPORATION) (outside diameter: 0.014 inches) which was previously inserted in the working lumen of the bronchoscope. The tip of this guide wire was advanced to the vicinity of the aimed alveolar parenchyma 3 affected with emphysema with the help of X ray fluoroscopy. Then, the catheter was advanced along the guide wire to the vicinity of the aimed alveolar parenchyma 3 affected with emphysema with the help of X ray fluoroscopy. Finally, the guide wire was pulled out.

As shown in FIG. 4B, the balloon 1a was expanded with air by means of the indeflator connected to the lumen for balloon expansion arranged at the base end of the catheter 1, so that the bronchiole 2 was closed. Hyaluronic acid as the polymeric electrolyte (A) 24, which had previously been filled into a syringe, was injected into the lumen of the alveolar parenchyma 3 affected with emphysema through the lumen of the catheter 1 from the syringe. Injection of the hyaluronic acid was suspended when the injection pressure of the syringe increased. Next, an excess amount of the hyaluronic acid was removed by suction. The steps for injection and removal of hyaluronic acid were repeated several times. Then, the balloon 1a, which had kept closed the bronchiole 2, was shrunk so that the bronchiole 2 had communications with the outside. This step formed the coating film 25 of hyaluronic acid as the polymeric electrolyte (A) 24 on the surface of the tissue of the alveolar parenchyma 3 affected with emphysema. (FIG. 4C)

Next, as shown in FIG. 4D, the balloon 1a was expanded again with air by means of the indeflator connected to the lumen for balloon expansion arranged at the base end of the catheter 1, so that the bronchiole 2 was closed. Poly(N,N-dimethylaminopropylacrylamide) (having a weight-average-molecular weight of 10,000 to 500,000) was filled in the other syringe as the polymeric electrolyte (B) 26. The poly(N,N-dimethylaminopropylacrylamide) was injected into the lumen of the alveolar parenchyma suffering from emphysema using a syringe through the other lumen which are different from those used for injection of hyaluronic acid of the catheter 1. Injection of the poly(N,N-dimethylaminopropylacrylamide) was suspended when the injection pressures of the syringe increased. The poly(N,N-dimethylaminopropylacrylamide), which has been injected into the lumen of the alveolar parenchyma 3, rapidly reacted for curing with the hyaluronic acid which had previously formed the film 25 on the surface of the tissue of the alveolar parenchyma 3 suffering from emphysema (FIG. 4D).

After injection, the poly(N,N-dimethylaminopropylacrylamide) was allowed to stand for five minutes for reacting sufficiently with the hyaluronic acid, thereby forming the ion complex film 27, and then the excess portion of the poly(N,N-dimethylaminopropylacrylamide) was removed by suction. After that, air which has lower viscosity than the hyaluronic acid and poly(N,N-dimethylaminopropylacrylamide) was injected from the forward end of the catheter 1 so that the polymeric electrolyte (B) 26 formed a uniform film on the surface of the alveolar parenchyma 3 suffering from emphysema (FIG. 4E).

The alveolar parenchyma 3 suffering from emphysema was evacuated by suction through the catheter 1 so that the volume of the alveolar parenchyma 3 suffering from emphysema was decreased. At this time, the decreased volume of the alveolar parenchyma 3 suffering from emphysema was maintained for a long period of time as the reaction between hyaluronic acid and poly(N,N-dimethylaminopropylacrylamide) proceeded and the cross-linking reaction in the ion complex film proceeded accordingly (FIG. 4F).

The invention claimed is:

1. A method for treatment of emphysema in a patient in need thereof, comprising:
   (a) inserting a catheter into a bronchus or bronchiole of the patient to reach a respiratory region comprising pulmonary alveoli or alveolar sacs, the respiratory region including an inner wall;
   (b(i)) injecting air into the respiratory region through the catheter at an air injection pressure;
   (b(ii)) injecting a film-forming agent into the respiratory region through the catheter while maintaining the air injection pressure, thereby forming a film on the inner wall of the respiratory region, wherein step (b(ii)) comprises
   (b-1) injecting the film-forming agent, which is a viscous polymer solution, into the respiratory region through the catheter and then removing by suction an excess of the viscous polymer solution;
   (b-2) injecting the film-forming agent, which is a material capable of curing upon reaction with water or divalent metal ions, into the respiratory region through the catheter, allowing the material to react with water or divalent metal ions present on the surface of the respiratory region, and then removing by suction an excess of the material; or
   (b-3) injecting a first polymeric electrolyte having a charge into the respiratory region through the catheter and then removing by suction an excess of the first polymeric electrolyte, thereby allowing the first polymeric electrolyte to form a coating film on the inner wall of the respiratory region, and then injecting a second polymeric electrolyte, which has a charge opposite to the charge of the first polymeric electrolyte, into the respiratory region through the catheter, thereby allowing the second polymeric electrolyte to contact the coating film of the first polymeric electrolyte, and then removing by suction an excess of electrolyte, and finally removing by suction an excess of the first polymeric electrolyte, with the first polymeric electrolyte and the second polymeric electrolyte serving as the film-forming agent and
   (c) shrinking the pulmonary alveoli or alveolar sacs.

2. The method of claim 1, wherein
   the catheter has a balloon, and
   step (b(i)) further includes an additional substep of closing the bronchus or bronchiole by expanding the balloon attached to the catheter prior to injection of the film-forming agent.

3. The method of claim 2, wherein the step (b(ii)) comprises the steps of (b-3), and further comprising, after removal by suction of the excess of the second polymeric electrolyte, injecting the first polymeric electrolyte into the respiratory region through the catheter, and finally removing by suction an excess of the first polymeric electrolyte, with the first polymeric electrolyte and the second polymeric electrolyte serving as the film-forming agent.

4. The method of claim 3, wherein the step (c) for shrinking the pulmonary alveoli or alveolar sacs is carried out by any of:
- (c-1) filling a reactive gas into the pulmonary alveoli or alveolar sacs through the catheter, and then closing the bronchus or bronchiole by a means to close a bronchus or bronchiole and injecting a gas absorbing agent that absorbs the reactive gas into the pulmonary alveoli or alveolar sacs;
- (c-2) after the step (b) in which the film-forming agent is one capable of forming a foam-like film, then allowing the foams of the film-forming agent to disappear or removing by suction the foam-like film-forming agent through the catheter; or
- (c-3) removing by suction residual gas from the pulmonary alveoli or alveolar sacs through the catheter.

5. The method of claim 1, wherein the catheter has a balloon in the center side, and the injection of the film-forming agent is at a constant pressure and is preceded by injecting air through the catheter into the respiratory region while maintaining a constant pressure.

6. The method of claim 1, wherein the step (c) for shrinking the pulmonary alveoli or alveolar sacs is carried out by any of:
- (c-1) filling a reactive gas into the pulmonary alveoli or alveolar sacs through the catheter, and then closing the bronchus or bronchiole by a means to close a bronchus or bronchiole and injecting a gas absorbing agent that absorbs the reactive gas into the pulmonary alveoli or alveolar sacs;
- (c-2) after the step (b) in which the film-forming agent is one capable of forming a foam-like film, then allowing the foams of the film-forming agent to disappear or removing by suction the foam-like film-forming agent through the catheter;
- (c-3) removing by suction residual gas from the pulmonary alveoli or alveolar sacs through the catheter; or
- (c-4) removing by suction the film-forming agent through the catheter.

7. The method of claim 1, wherein the step (c) for shrinking the pulmonary alveoli or alveolar sacs is carried out by any of the steps (b-1) to (b-3) and optionally by any of:
- (c-1) filling a reactive gas into the pulmonary alveoli or alveolar sacs through the catheter, and then closing the bronchus or bronchiole by a means to close a bronchus or bronchiole and injecting a gas absorbing agent that absorbs the reactive gas into the pulmonary alveoli or alveolar sacs;
- (c-2) after the step (b) in which the film-forming agent is one capable of forming a foam-like film, then allowing the foams of the film-forming agent to disappear or removing by suction the foam-like film-forming agent through the catheter; or
- (c-3) removing by suction residual gas from the pulmonary alveoli or alveolar sacs through the catheter.

* * * * *